United States Patent
Schultz

(10) Patent No.: US 10,107,403 B2
(45) Date of Patent: Oct. 23, 2018

(54) PINCH FLOW REGULATOR

(71) Applicant: LIFE TECHNOLOGIES CORPORATION, Carlsbad, CA (US)

(72) Inventor: Jonathan Schultz, Guilford, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/407,333

(22) Filed: Jan. 17, 2017

(65) Prior Publication Data

US 2017/0191571 A1 Jul. 6, 2017

Related U.S. Application Data

(60) Division of application No. 15/162,876, filed on May 24, 2016, now Pat. No. 9,579,654, which is a continuation of application No. 14/740,573, filed on Jun. 16, 2015, now Pat. No. 9,375,716.

(60) Provisional application No. 62/013,471, filed on Jun. 17, 2014.

(51) Int. Cl.
| | |
|---|---|
| *B01L 3/00* | (2006.01) |
| *F16K 7/07* | (2006.01) |
| *G05D 16/06* | (2006.01) |

(52) U.S. Cl.
CPC .............. *F16K 7/07* (2013.01); *B01L 3/567* (2013.01); *G05D 16/0638* (2013.01)

(58) Field of Classification Search
CPC ..................................................... B01L 3/567
See application file for complete search history.

(56) References Cited

U.S. PATENT DOCUMENTS

| | | | |
|---|---|---|---|
| 7,143,785 B2 | 12/2006 | Maerkl et al. | |
| 7,842,248 B2 | 11/2010 | McAvoy et al. | |
| 7,887,756 B2 | 2/2011 | McAvoy et al. | |
| 7,892,496 B2 | 2/2011 | McAvoy et al. | |
| 8,092,761 B2 | 1/2012 | McAvoy et al. | |
| 8,220,494 B2 | 7/2012 | Studer et al. | |
| 8,584,703 B2 | 11/2013 | Kobrin et al. | |

(Continued)

FOREIGN PATENT DOCUMENTS

| | | |
|---|---|---|
| FR | 1507301 | 12/1967 |
| GB | 870257 | 6/1961 |

OTHER PUBLICATIONS

PCT/US2015/036071, International Search Report and Written Opinion of the International Searching Authority, Oct. 2, 2015, 10 pages.

*Primary Examiner* — Jyoti Nagpaul

(57) ABSTRACT

A valve for regulating fluid flow includes a housing base defining a lower cavity and comprising a pinch structure within the lower cavity, a gas inlet providing external access to the lower cavity, a base fluid inlet, and a base fluid outlet. A housing cover defines an upper cavity and comprises a cover fluid inlet and a cover fluid outlet. The cover fluid inlet is in fluidic communication with the base fluid outlet between the upper cavity and the lower cavity, and the cover fluid outlet provides external access from the upper cavity. A diaphragm is disposed between the housing base and the housing cover. A pinch plate is disposed in the lower cavity and comprises a pinch point disposed opposite the pinch structure. A pinch tube is in fluidic communication between the base fluid inlet and the base fluid outlet in the lower cavity.

20 Claims, 19 Drawing Sheets

(56) References Cited

U.S. PATENT DOCUMENTS

| | | |
|---|---|---|
| 8,763,642 B2 | 7/2014 | Vangbo |
| 9,375,716 B2 | 6/2016 | Schultz |
| 9,579,654 B2 * | 2/2017 | Schultz .................. B01L 3/567 |
| 2012/0181460 A1 | 7/2012 | Eberhart et al. |
| 2013/0280702 A1 | 10/2013 | Schultz et al. |

* cited by examiner

PINCH FLOW REGULATOR

CROSS-REFERENCE TO RELATED APPLICATION(S)

This application is a divisional of U.S. application Ser. No. 15/162,876 filed May 24, 2016, which is a continuation of U.S. application Ser. No. 14/740,573 filed Jun. 16, 2015 (now U.S. Pat. No. 9,375,716), which claims benefit of U.S. Provisional Application No. 62/013,471 filed Jun. 17, 2014, which are incorporated herein by reference in their entirety.

TECHNICAL FIELD

This application relates to the field of fluidic flow control, and in particular, to pinch valve regulators.

BACKGROUND

Conventional valves have been used to regulate fluid pressure and flow in different applications. In some applications, a lengthy tube having a small inner diameter have been used to regulate fluid pressure, such as in fluidic systems that direct flow of reagents through a flow cell containing a sensor array. Long tubes and multiple valves have conventionally been employed in these systems to discard reagents after exiting a flow cell and sensor array. However, as the length of a tube increases, so does the possibility of clogs within the tube, as well as the cost to manufacture a lengthy tube having a desired precision. In addition, variance in the inner diameter of such tubes leads to reduced accuracy when controlling fluid flow and leads to difficulty in calibrating fluid flow systems. In view of the above, it would be advantageous to have a device for regulating fluid flow which overcame the deficiencies of current approaches.

SUMMARY

Methods and devices for controlling fluid flow, such as methods and devices for generating a fixed flow rate having a linear response to a control gas pressure, are described. In various implementations, the methods or devices may be used in a chemical or biological system, for example, including a sensor in fluidic communication to provide precise and consistent fluid flow to provide fluid flows in and out of the sensor. The methods or devices are exemplified in a number of implementations, some of which are summarized below and throughout the specification.

BRIEF DESCRIPTION OF THE DRAWINGS

In order to understand the invention and to see how it may be carried out in practice, implementations will now be described, by way of non-limiting example only, with reference to the accompanying drawings, in which.

DETAILED DESCRIPTION

Reference will now be made in detail to implementations, examples of which are illustrated in the accompanying drawings. In the following detailed description, numerous specific details are set forth in order to provide a sufficient understanding of the subject matter presented herein. But it will be apparent to one of ordinary skill in the art that the subject matter may be practiced without these specific details. Moreover, the particular implementations described herein are provided by way of example and should not be used to limit the scope of the invention to these particular implementations. In other instances, well-known structures and components have not been described in detail so as not to unnecessarily obscure aspects of the implementations of the invention.

A system includes a pinch valve regulator for controlling reagent flow within the system. In particular, the pinch valve regulator can provide regulated flow at low flow rates and finds particular use in regulating effluent flow rates. Alternatively, the pinch valve regulator can be disposed within an inlet flow or in the path of other fluid flows within the system. Such regulated low flow rates are particularly useful in chemical and biological systems utilizing expensive reagents. For example, the pinch valve regulator can find use in biological systems incorporating nucleotide reagent solutions, such as systems for amplification (e.g., polymerase chain reaction (PCR) or recombinase polymerase amplification (RPA)), sequencing, synthesis, or combinations thereof. In particular, such pinch valve regulators have use in regulating the flow of reagents including one or more types of nucleotides or analogs thereof. Such reagents can be used, for example, in sequencing by synthesis.

Figure 1:
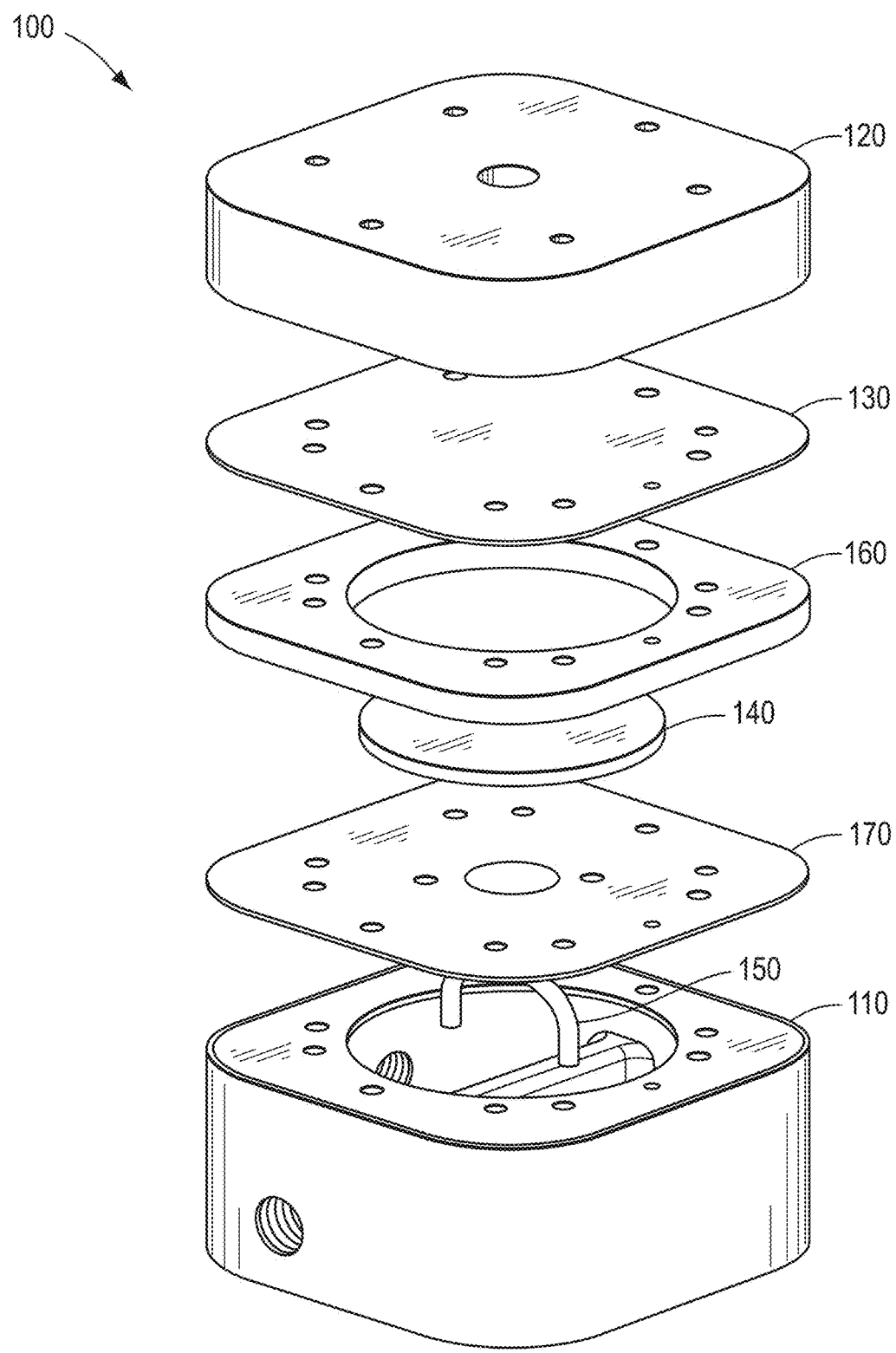
FIG. 1 is an exploded schematic view describing an example valve.

FIG. 1 provides an exploded schematic view of an example pinch valve regulator 100. The valve 100 includes a housing base 110 and a housing cover 120 disposed above the base 110. A diaphragm 130 is disposed between the housing base 110 and the housing cover 120. A pinch plate 140 is disposed between the diaphragm 130 and the base 110. In operation, the pinch plate 140 moves relative to the housing base 110 to pinch a pinch tube 150 against a pinch structure (as illustrated more clearly in FIGS. 2, 3A and 3B) to restrict fluid flow through the pinch tube 150. One or more gaskets 160, 170 can be disposed between the housing base 110 and housing cover 120 to prevent fluid leakage and to ensure smooth valve operation.

Figure 2:
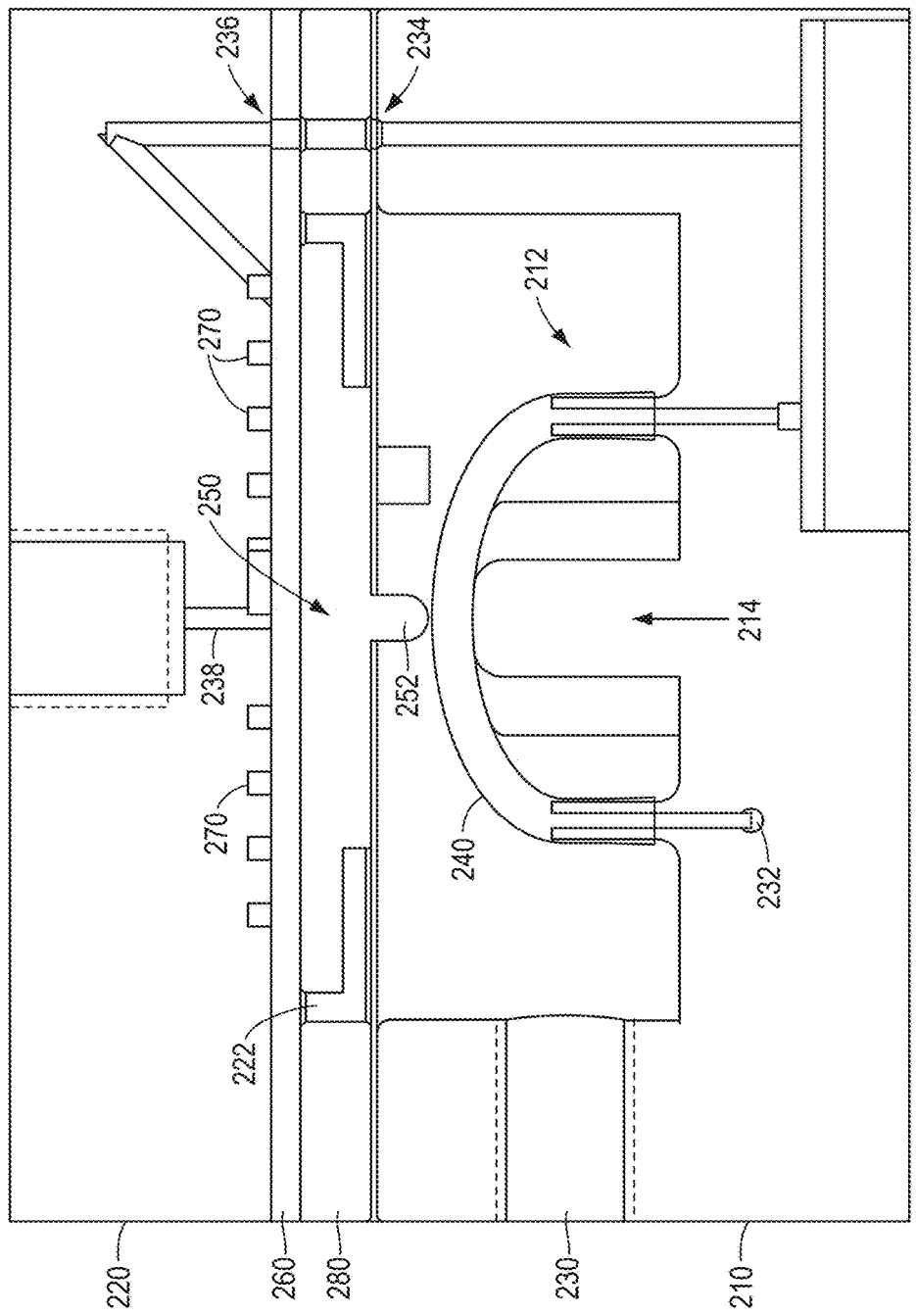
FIG. 2 is a cross-sectional schematic view describing an example valve.

FIG. 2 provides a cross-sectional schematic view of an example pinch valve regulator. A valve 200 includes a housing base 210 and a housing cover 220 disposed over of the base 210. The housing base 210 includes a lower cavity 212 and a pinch structure 214 protruding within the lower cavity 212. The housing base 210 includes a gas inlet 230, providing external access to the lower cavity 212. A base fluid inlet 232 provides an external access path that is connected to one end of a pinch tube 240 within the lower cavity 212. The other end of a pinch tube 240 is connected to a base fluid outlet 234. Accordingly, the pinch tube 240 provides fluidic communication between the base fluid inlet 232 and the base fluid outlet 234. The pinch tube 240 extends between the pinch structure 214 and a pinch point 252 of a pinch plate 250.

In an example, the pinch structure 214 includes a rectangular prism extending into the lower cavity 212. As illustrated, the rectangular prism as a rounded top. In another example, the rectangular prism can have a flat top. Alternatively, the prism can have a pointed structure, such as a triangular prims. In general, the pinch structure 214 forms a counter structure to which the pinch point 252 can secure and punch the pinch tube 240.

The base fluid outlet 234 is in turn connected to and provides fluidic communication with a cover fluid inlet 236 between the upper cavity and the lower cavity to provide a fluid path through the housing base 210 and the housing cover 220. The cover fluid inlet 236 is in fluidic communication with a cover fluid outlet 238 via a fluid path 270. The cover fluid outlet 238 provides external access to the fluid path 270 from the housing cover 220. A diaphragm 260 is disposed between the housing base 210 and the housing cover 220 to fluidically separate the lower cavity 212 from an upper cavity 222 defined between the cover 220 and the diaphragm 260.

The housing cover 220 defines an upper cavity 222 where the fluid path 270 is disposed. Optionally a gasket 280 can define part of the lower cavity 212 or part of the upper cavity 222. The pinch plate 250 can be disposed within the cavity region defined by the housing cover 220 or the gasket 280. The base fluid outlet 234 and the cover fluid inlet 236 are in fluidic communication through the gasket 280 and diaphragm 260. Alternatively, the base fluid outlet 234 and the cover fluid inlet 236 can be fluidically connected external to the housing base 210 or the housing cover 220. The diaphragm 260 provides separation between the lower cavity 212 and the upper cavity 222. A pinch plate 250 is disposed within the cavities 212, 222 defined within the housing cover 220 and the housing base 210. The pinch plate 250 includes a pinch point 252 that is disposed opposite the pinch structure 214. The pinch point 252 is illustrated with a rounded tip. Alternatively, the pinch point 252 can have a sharp tip. The pinch plate 250 moves relative to the housing base 210 to pinch the pinch tube 240 to restrict fluid flow through the pinch tube 240 based on fluid pressure within the fluid path 270 and gas pressure within the lower cavity 212.

Figure 3A:
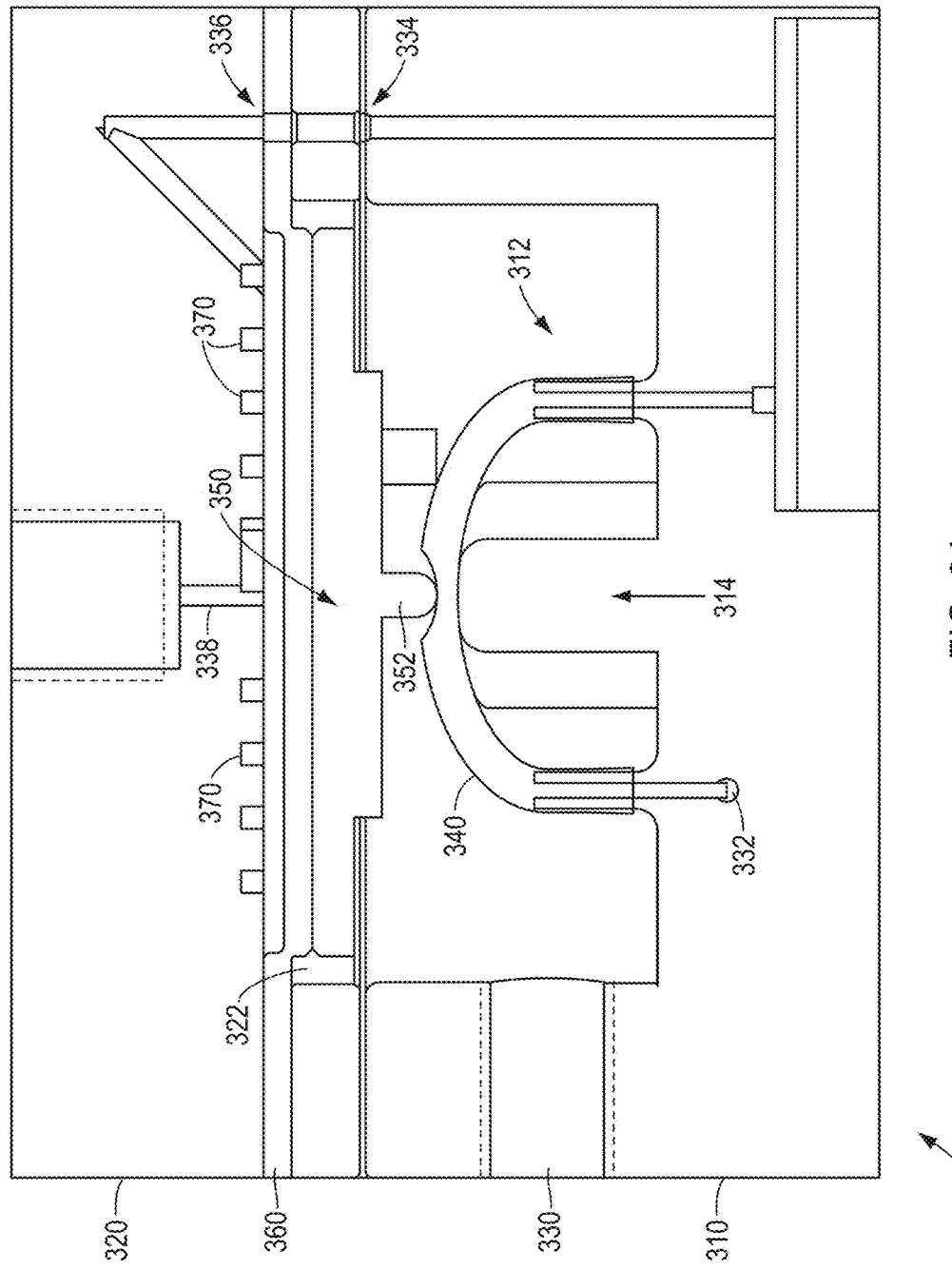
FIG. 3A is a cross-sectional schematic view describing an example valve.
Figure 3B:
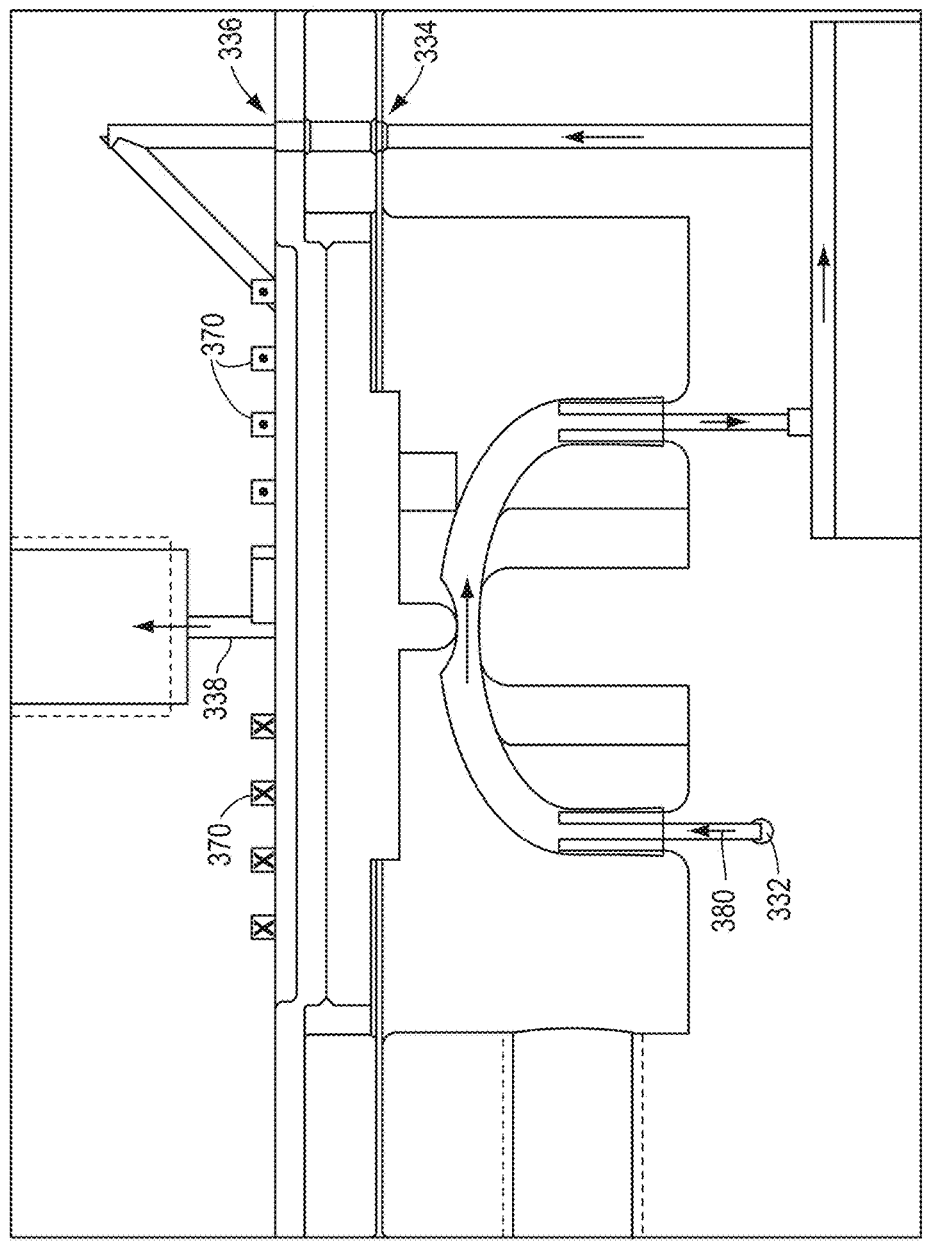
FIG. 3B is a cross-sectional schematic view describing an example valve.

The valves described herein operate to regulate fluid flow as a function of gas pressure within the lower cavity. FIG. 2 illustrates a valve structure prior to applying fluid into the valve 200 and FIGS. 3A-3B illustrate an equilibrium state of a valve where fluid flows through valve 300 at a flow rate based on the input gas pressure. An implementation of the pinch valve in operation will be described below with reference to FIGS. 2 and 3A-3B.

Gas pressure is applied to a gas inlet 230, 330 of the valve to pressurize the lower cavity 212, 312 at an input/reference gas pressure. The pressurized lower cavity applies an upward force against the pinch plate 250, 350 and diaphragm 260, 360 towards the housing cover 220, 320. Fluid is applied to the base fluid inlet 332 and flows sequentially through pinch tube 340, base fluid outlet 334, cover fluid inlet 336, fluid path 370, cover fluid outlet 338, and then out of the valve. The fluid flowing through the housing cover 320 applies a downward force against the diaphragm 360 and pinch plate 350 towards the housing base 310. As the fluid pressure in the fluid path 370 increases relative to the gas pressure in the lower cavity 312, the diaphragm 360 moves toward the housing base 310 and applies downward force against the pinch plate 350. In particular, the diaphragm 360 is to motivate the pinch point 352 relative to the pinch structure 314 in response to a difference between a fluid pressure in the upper cavity 322 and a gas pressure in the lower cavity 312. For instance, the diaphragm 360 is to motivate the pinch point 352 towards the pinch structure 314 in response to an increase in the fluid pressure within the upper cavity 322 relative to the gas pressure in the lower cavity 312 to restrict fluid flow in the pinch tube 340.

As the pinch plate 350 moves toward the housing base 310, the pinch point 352 applies a downward force onto pinch tube 340 so as to pinch the tube 340 against the pinch structure 314 and restrict fluid flow or cause a pressure drop across the punch tube 340 and in the upper cavity 322 until the input gas pressure counteracts the fluid pressure in the upper cavity 322 to thereafter provide a constant fluid flow rate from the valve 300. FIG. 3B illustrates a valve 300 with directional arrows 380 indicating the fluid flow path through the valve 300.

The pinch actuation force of the diaphragm driven pinch valve is such that the output fluid pressure is regulated by the input gas pressure. By setting the pressure in the lower gas cavity 312 to a known value, fluid flow and pressure exiting the housing cover 320 is controlled. In this manner, the valve self-regulates to reach equilibrium and can provide a desired constant fluid flow. In summary, the output fluid pressure at the cover fluid outlet follows the input gas pressure at the gas inlet and can be independent of the fluid pressure at the base fluid inlet. These features are disclosed in greater detail with respect to FIG. 9.

Figure 4:
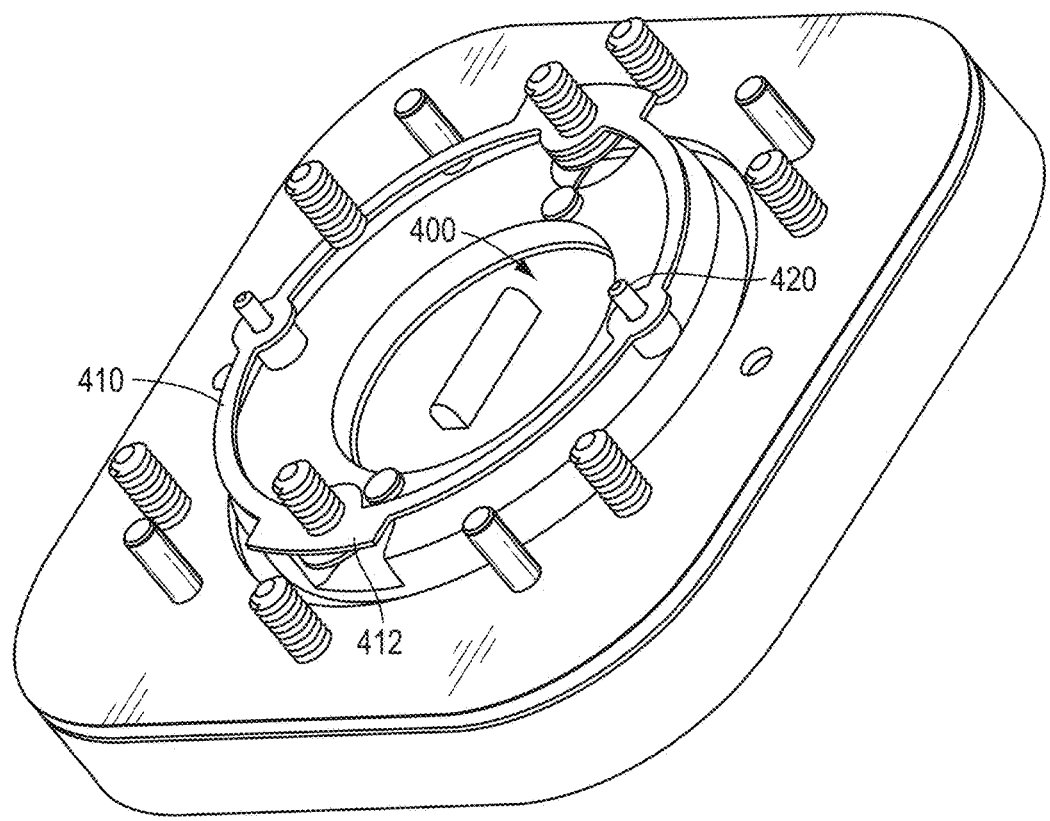
FIG. 4 is a schematic view describing an example valve.

In various implementations, a valve includes a resilient structure which is in contact with and provides lateral support to a pinch plate. FIG. 4 provides a cross-sectional perspective view of the valve including the housing cover 430 with the housing base portion removed. A pinch plate 400 is provided, and a resilient structure 410 is disposed within the lower cavity of the housing base. The resilient structure 410 can include a spring, such as a flat spring, or a die cut flat polymer ring. The resilient structure 410 can attach to at least one pair of posts 420 positioned on laterally opposite sides of the pinch plate 400. A plurality of posts can be positioned along a circumference of the pinch plate 400. The resilient structure 410 engages the at least one pair of posts 420 to provide the lateral support, but provides limited vertical resistance. As fluid pressure from the housing cover pushes downward on the pinch plate 400, the resilient structure 410 counters any undesirable lateral movement of the pinch plate 400 to maintain a balanced pinch plate 400 and can prevent the pinch point from skewing relative to the pinch structure.

FIGS. 5-8 are directed to various implementations of a housing cover of the valve, and in particular, the structures related to the fluid path and the diaphragm. As fluid flows from the base fluid outlet of the housing base and into the cover fluid inlet, the housing cover defines a fluid path having a lower area open to the upper cavity. The fluid path is in fluidic communication between the cover fluid inlet and the upper cavity and between the upper cavity and the cover fluid outlet. Fluid flows through the fluid path and out of the housing cover through the cover fluid outlet. In various implementations, fluid flow in the upper cavity of the housing cover flows through a fluid path and is distributed over the diaphragm. Optionally, a filter, mesh, porous sheet, or perforated membrane is disposed between the fluid path and the diaphragm to prevent extrusion of the diaphragm into the fluid path and occlusion of the fluid path by the diaphragm. The filter, mesh, porous or patterned sheet, or perforated or patterned membrane can further assist with distributing fluid pressure across the surface area of the diaphragm, providing force on the pinch plate.

Figure 5:
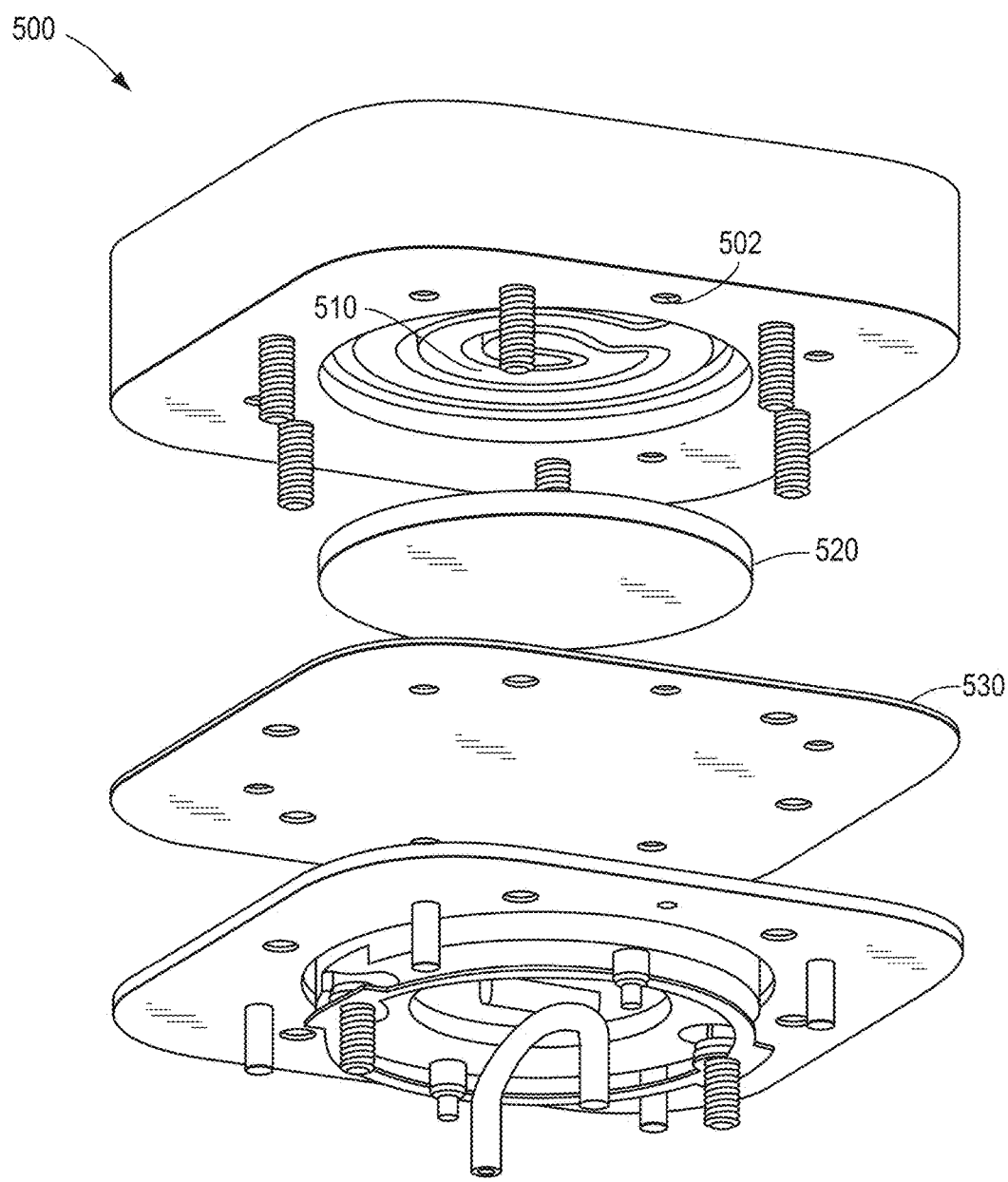
FIG. 5 is an exploded schematic view describing an example valve.

FIG. 5 provides an exploded schematic view of an example housing cover 500, fluid path 510, pressure distributor 520 and diaphragm 530. The housing cover 500 defines a fluid path 510 in fluidic communication with the upper cavity. In particular, the housing cover 500 defines a fluid path 510 having a lower area open to the upper cavity. The fluid path 510 of FIG. 5 extends between a cover fluid inlet 502 and a cover fluid outlet 504. The fluid path 510 is in fluidic communication between the cover fluid inlet and the upper cavity, as well as between the upper cavity and the cover fluid outlet. As illustrated, the fluid path 510 within the housing cover 500 can have a spiral configuration that allows fluid to flow within a spiral fluid channel. Such a configuration provides fluid flow over a larger surface area of the diaphragm 530 to provide balanced and even downward pressure to a pinch plate. Alternatively, the fluid path can have a shape other than a spiral shape, and can have any configuration that provides fluid flow over the diaphragm 530. For example, the fluid path can provide a set of channels, such as straight channels, wavy channels, concentric circles, or any combination thereof.

As illustrated in FIG. 5, fluid enters the fluid path 510 from the cover fluid inlet 502 along the perimeter and exits the cover fluid outlet 504 at a position over the location where the pinch point and pinch structure pinches the pinch tube. The pressure distributor 520 can be disposed in the upper cavity of the housing cover 500 between the fluid path 510 and the diaphragm 530 to further distribute fluid flow from the fluid path 510 over the diaphragm 530 and limit encroachment of the diaphragm 530 into the fluid path 510. As fluid flow initially travels through the spiral fluid path, before the diaphragm 530 is pushed down, the pressure distributor 520 allows fluid to spread across the diaphragm 530.

The pressure distributor 520 can be a filter, such as a sintered metal filter or a sintered ceramic frit, or can be a mesh structure, such as a wire or polymer mesh. The filter or mesh can include pores or small open areas on its surface allowing fluid flowing through fluid path 510 to seep out from the fluid path 510 and flow over substantially the entire surface area of the pressure distributor 520 and diaphragm 530, as opposed to just the fluid path 510. While much of the fluid in the fluid path 510 stays within the spiral channel, fluid will spread out over the filter or mesh via the pores or openings to distribute fluid pressure. In an example, the filter or mesh provides further consistency in providing downward pressure on the diaphragm 530 and pinch plate. In addition or alternatively, the filter or mesh can prevent extrusion of the diaphragm into the fluid path that would limit fluid flow within the fluid path, particularly when initially starting fluid flow.

Figure 6:
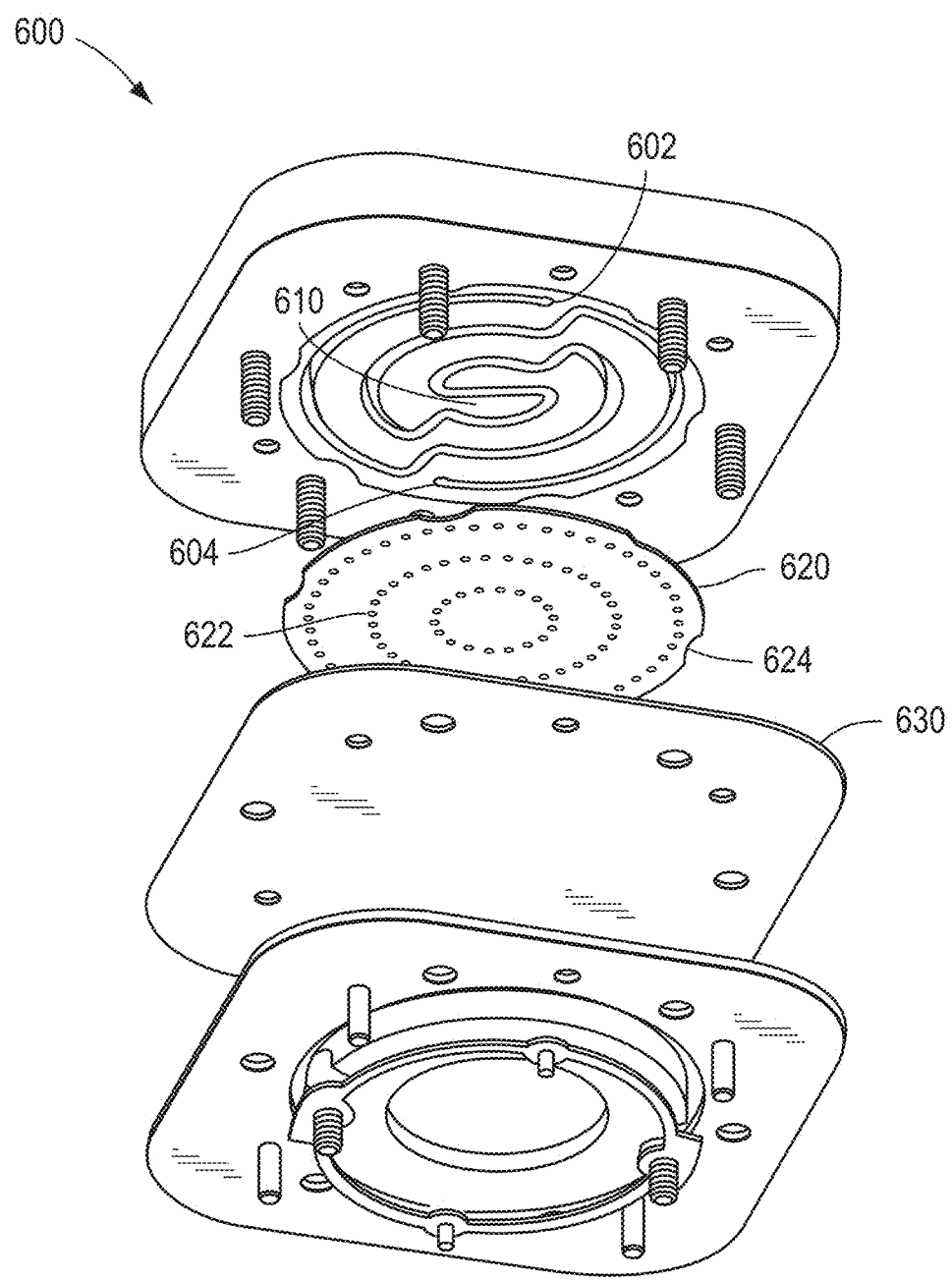
FIG. 6 is an exploded schematic view describing an example valve.

FIG. 6 provides an exploded schematic view of an example housing cover 600, fluid path 610, pressure distributor 620 and diaphragm 630. The fluid path 610 of FIG. 6 extends from the cover fluid inlet 602 to the cover fluid outlet 604. The fluid path 610 has a spiral-like configuration that provides fluid flow over a large surface area of the diaphragm 630 to provide balanced or even downward pressure to a pinch plate. A pressure distributor 620 can be disposed in the upper cavity of the housing cover 600 between the fluid path 610 and the diaphragm 630 to further distribute fluid flow over the diaphragm 630. In particular, the pressure distributor 620 can prevent the diaphragm 630 from encroaching into the fluid path 610 and limiting fluid flow within the fluid path 610.

In FIG. 6, the pressure distributor 620 is a membrane disposed between the diaphragm 630 and the fluid path 610. The membrane includes a plurality of small holes or openings 622 underneath the channels of the fluid path 610. For example, the fluid path 610 in FIG. 6 has a spiral configuration that forms concentric circles. Accordingly, the membrane 620 includes a plurality of small holes 622 forming concentric circles corresponding to the spiral fluid path 610. In other examples, the membrane 620 can include a plurality of small holes following the pattern of the fluid path 610, such as spiral configurations, concentric circles, straight lines, wavy lines, a regular or irregular array, or any combination thereof. The membrane 620 with small holes 622 allows fluid flowing through fluid path 610 to seep out from the fluid path 610 and flow over substantially the entire surface area of the pressure distributor 620 and diaphragm 630, as opposed to just the fluid path 610. While most of the fluid in the fluid path 610 stays within the spiral channel, some fluid spreads out over the diaphragm 630 via the holes 622 to distribute fluid pressure. The use of a membrane 620 provides further consistency in providing downward pressure on the diaphragm 630 and a pinch plate.

The housing cover 600 can include a plurality of fasteners 608 for assembly with corresponding fastener holes in a housing base to fasten the housing cover to the housing base. The edges of the pressure distributor 620 can be scalloped or have projections 624 corresponding to the shape of the fastener 608 for aligned seating of the distributor 620 and prevent rotation. The fluid path and diaphragm can also define scalloped projections.

In various implementations, the membrane 620 includes a sheet having a thickness in a range of 0.005 inches to 0.5 inches, such as approximately 0.01 inches, with holes having an average diameter in a range of 0.001 inches to 0.01 inches, such as approximately 0.006 inches. The pressure distributor 620 can be machined or die cut for ease of manufacture and reduction of cost.

Figure 7A:
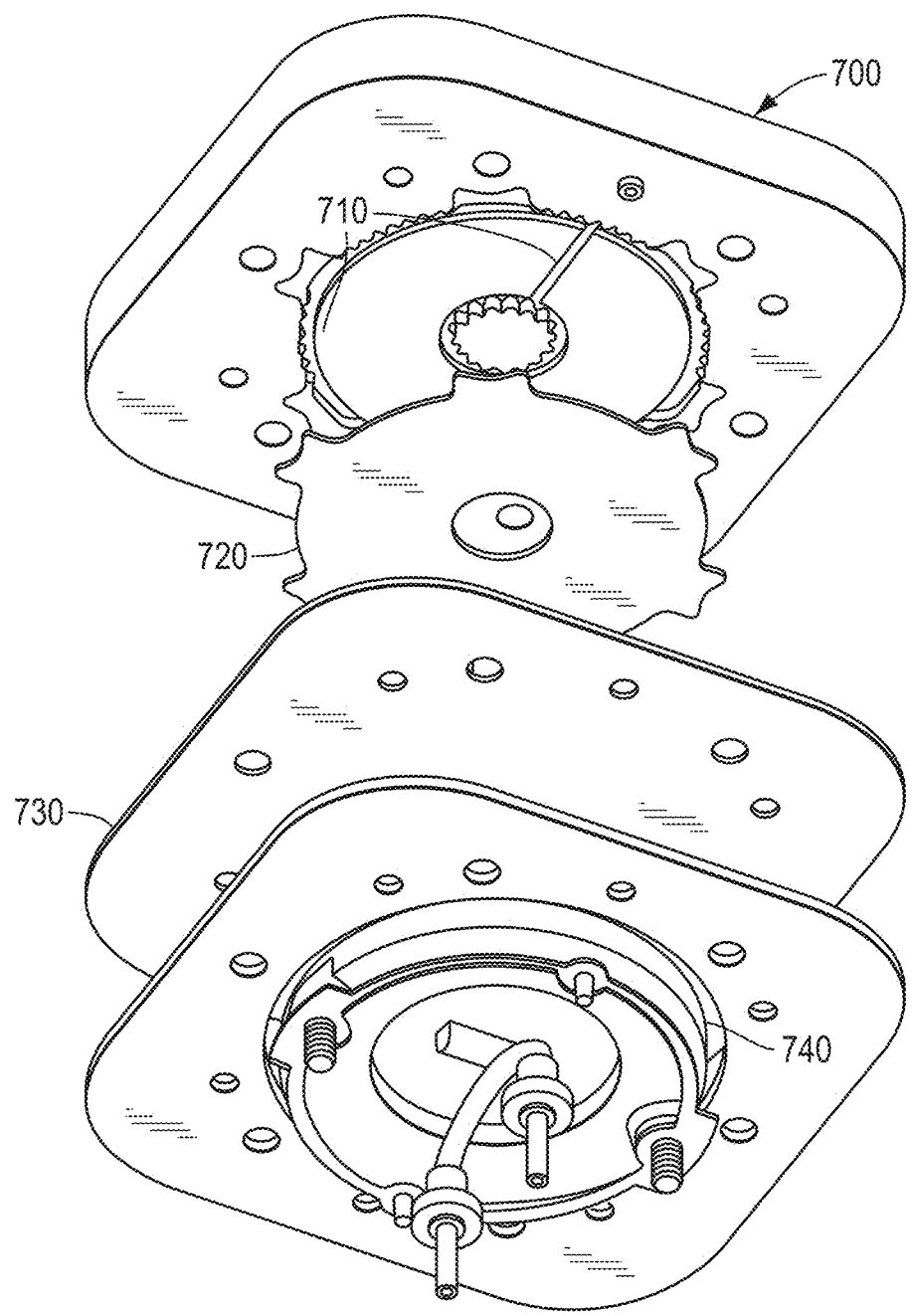
FIG. 7A is an exploded schematic view describing an example valve.

FIG. 7A provides an exploded schematic view of an example housing cover 700, fluid path 710, pressure distributor 720 and diaphragm 730. The pressure distributor 720 is disposed between fluid path 710 and diaphragm 730. Fluid flow through the fluid path 710 is distributed by the pressure distributor 720 over a large surface area of the diaphragm 730 to provide a balanced downward pressure on the diaphragm 730 and a pinch plate 740. The configurations described below allow the fluid path 710 and the pressure distributor 720 to be machined or die cut for ease of manufacture and reduction of cost.

Figure 7B:
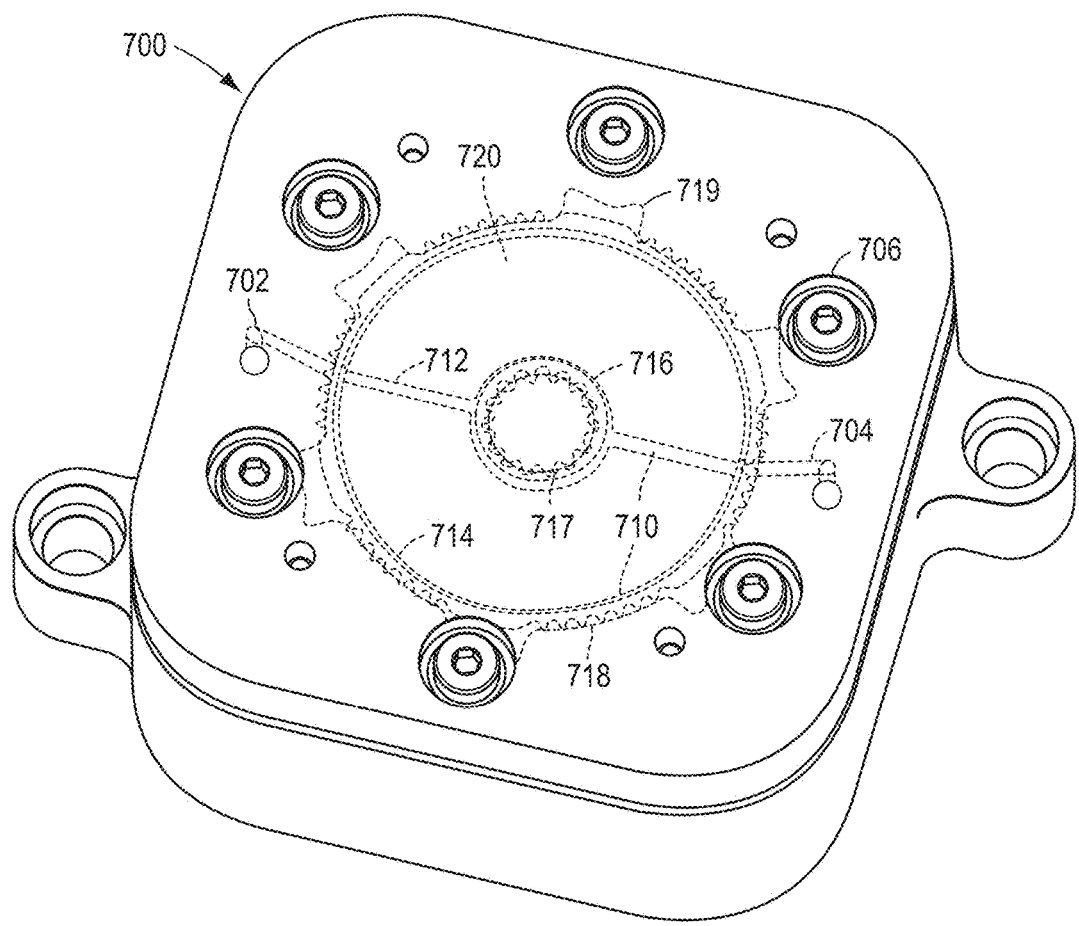
FIG. 7B is a perspective view describing an example assembled valve.

FIG. 7B is a bottom perspective view describing an example assembled valve. The fluid path 710 extends from the cover fluid inlet 702 to the cover fluid outlet 704. The fluid path 710 defines a lateral channel 712 and circular channels 714 along an outer perimeter. At the center of the fluid path 710, the lateral channel 712 opens up to provide fluid flow into and around an inner island 716. The inner island 716 defines a set of grooves or vertical channels 717. Fluid flows from the grooves or vertical channels 717 of the inner island 716 past the pressure distributor 720 to distribute fluid over the diaphragm 730. Likewise, the circular channel 714 defines a set of grooved vertical channels 718 along the outer edges of the fluid path 710. The pressure distributor 720 is disposed over the circular channels 714, but allows fluidic communication between the fluid path 710 and the diaphragm 730 via the vertical channels 718.

Together, the fluid path 710 and pressure distributor 720 provide fluid flow over a large surface area of the diaphragm 730 to provide balanced or even downward pressure to a pinch plate or prevent the diaphragm 730 from encroaching into the fluid path 710. The pressure distributor 720 can also define projections 719 that fit around corresponding fasteners 706 to ensure proper seating and prevent rotation.

Figure 7C:
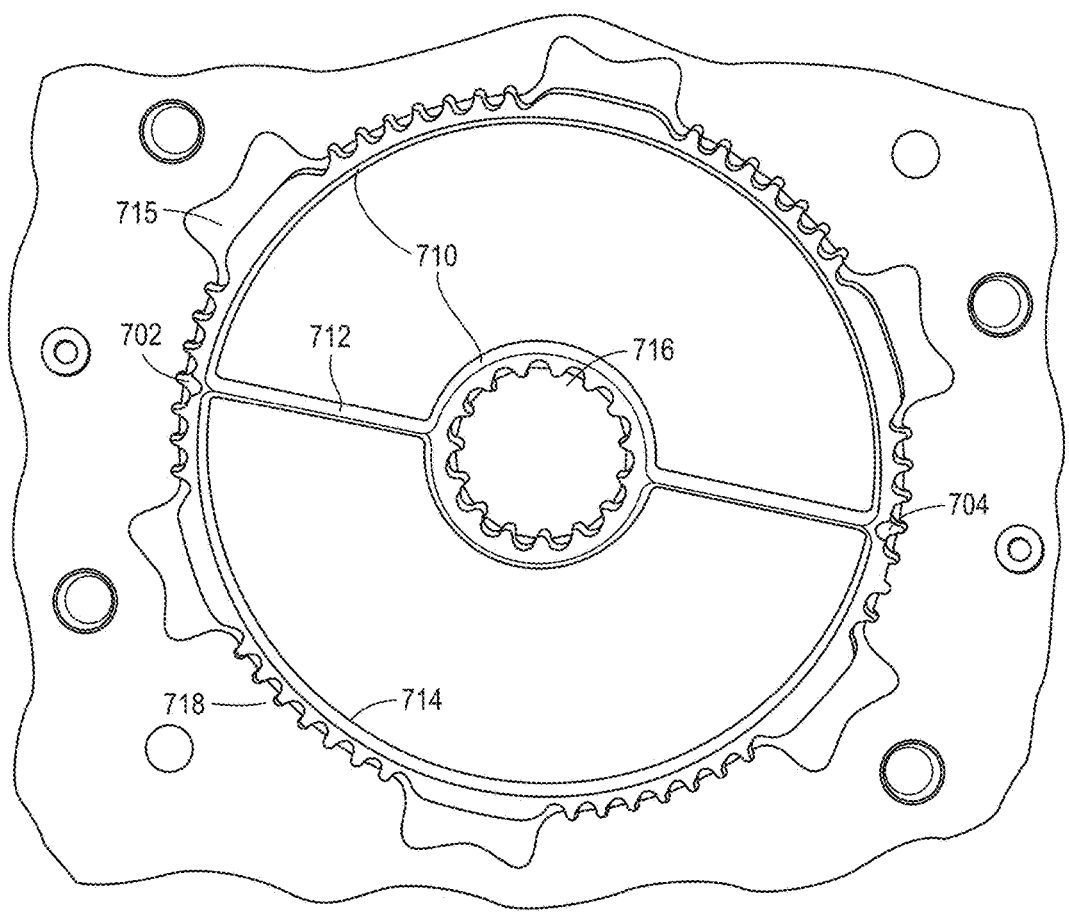
FIG. 7C is a perspective view describing an example fluid path.

FIG. 7C is a bottom perspective view describing an example fluid path. In particular, an underside of the fluid path 710 is illustrated and includes the cover fluid inlet 702, the cover fluid outlet 704, lateral channel 712, circular channels 714, inner island 716, and vertical channels 717, 718. As fluid pressure increases in the fluid path 710, transient pressure differences between the fluid flow within the channels 712, 714 and fluid adjacent the diaphragm causes fluid to move through the vertical channels 717, 718 and onto the diaphragm, providing a downward force on the diaphragm. When fluid flow into the valve is stopped, the upward pressure on the diaphragm pushes the fluid back into the channels 712, 714 via the vertical channels 717, 718, respectively. The housing cover 700 can include a plurality of recesses 715 into which the pressure distributor (e.g., the pressure distributor 720 of FIG. 7A and FIG. 7B) can fit to hold the filter in place.

Figure 7D:
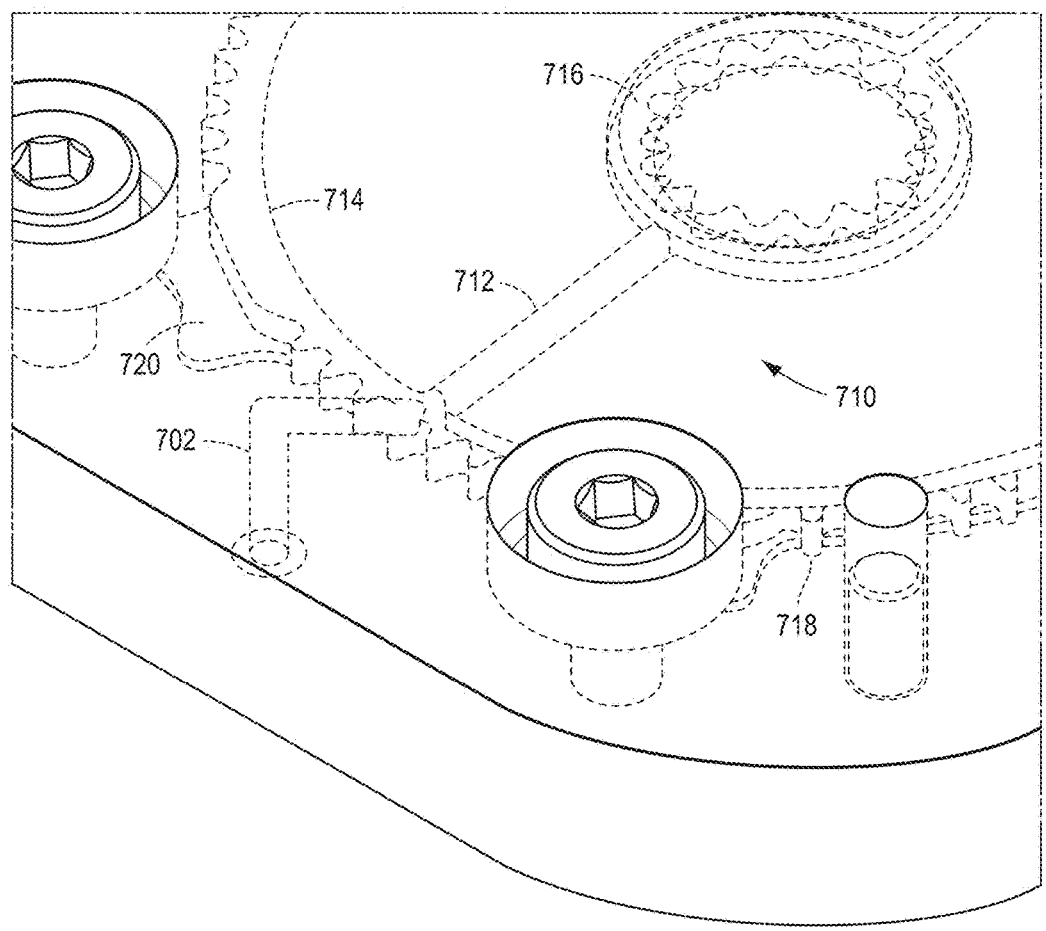
FIG. 7D is a detailed perspective view describing an example fluid path.

FIG. 7D is a detailed perspective view describing an example fluid path. The vertical channels 717, 718 are illustrated and show the pressure distributor 720 is disposed over portions of the channels 717, 718 and can allow fluid to distribute over the diaphragm (illustrated in FIG. 7A). The channels 712, 714 are covered by the pressure distributor 720.

Figure 7E:
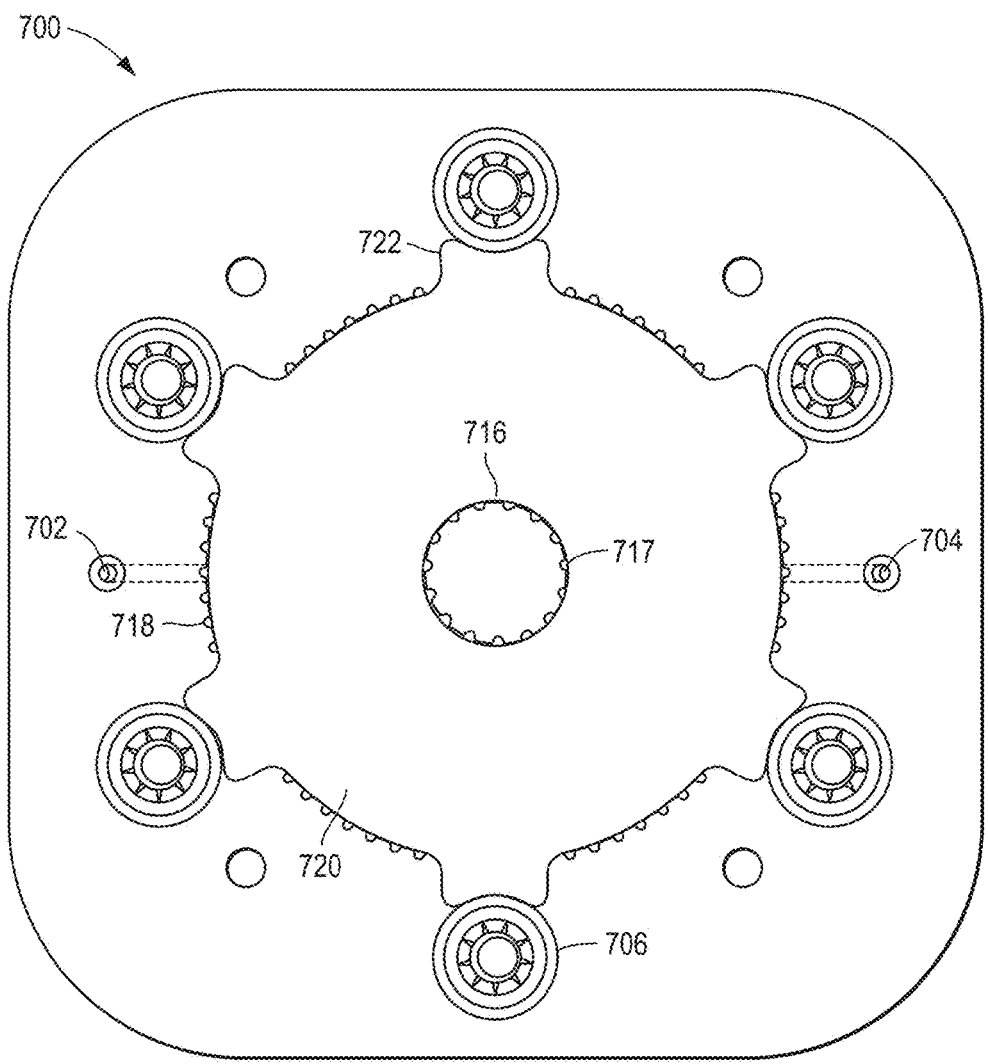
FIG. 7E is a plan view describing an example valve.

FIG. 7E is a bottom plan view of the housing cover 700 from the perspective of the housing base. As discussed above, the pressure distributor 720 is disposed over the lateral channel and circular channels such that fluid can flow out from the channels and onto the diaphragm, and the diaphragm does not encroach into the fluid path. The vertical channels 717, 718 are only partially covered by the pressure distributor 720 to allow fluid to distribute over the diaphragm (illustrated in FIG. 7A). As such, the pressure distributor 720 is disposed over the circular channel 714 and the lateral channel 712 (illustrated in FIG. 7B) and allows fluidic communication between the fluid path and the pressure distributor where the pressure distributor is disposed over a portion of the circular channel and the lateral channel. The pressure distributor 720 can also define projections 722 that are shaped corresponding to fasteners 706 to ensure proper seating and prevent rotation.

Figure 8A:
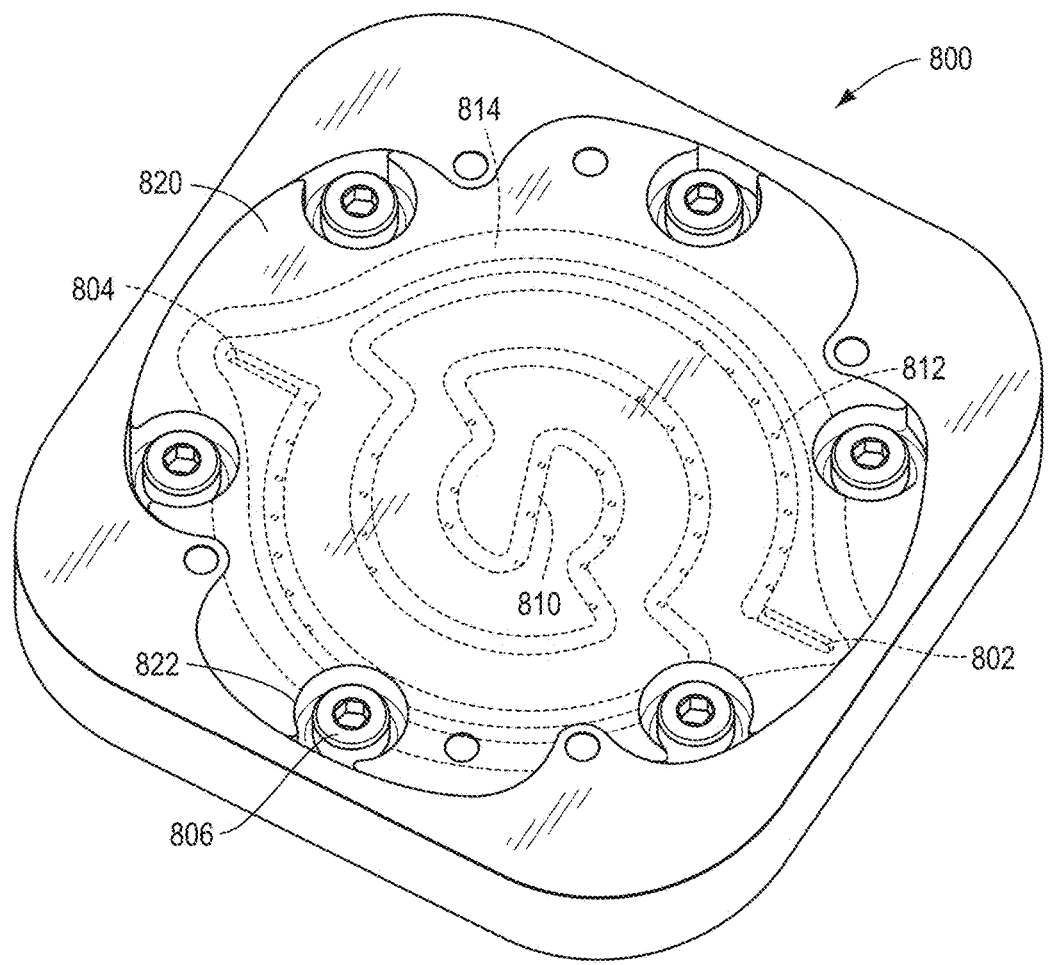
FIG. 8A is a perspective view describing an example assembled valve.

FIG. 8A is a top perspective view describing an example assembled valve including a housing cover 800, fluid path 810, and fluid path cover 820. The housing cover 800 is provided above a housing base and directly above a diaphragm without an intervening pressure distributor, such as a membrane or filter described above. The housing cover 800 includes a fluid path 810 that extends from a cover fluid inlet 802 to a cover fluid outlet 804. The fluid path 810 can have a spiral configuration that allows fluid to flow within a spiral fluid channel. This configuration provides fluid flow over a larger surface area of a diaphragm to provide balanced and even downward pressure to a pinch plate (not shown). The fluid path can have a shaper other than a spiral shape, and can have any configuration that provides fluid flow evenly over the diaphragm. The housing cover 800 defines a fluid path 810 in fluidic communication via openings or holes 812 with the upper cavity and is disposed opposite the upper cavity. While illustrated as circular holes, the openings can be circular, or can be slits, or alternatively can have a mesh pattern, or any combination thereof.

A fluid path cover 820 is placed over to cover the fluid path 810 to prevent fluid from seeping out above the channels of the fluid path 810. A gasket 814 can be provided as an additional barrier to prevent fluid from leaking out of the housing cover 800 and disposed between the fluid path cover 820 and the fluid path 810. The fluid path 810 includes a plurality of openings or holes 812 throughout the length of the fluid path 810 that are in fluidic communication between the fluid path and the diaphragm below housing cover 800. The holes 812 can be machined or die cut.

The housing cover 800 can include a plurality of fasteners 806 for assembly with corresponding fastener holes in a housing base and a housing cover. The edges of the fluid path cover 820 can be formed to include recesses 822 corresponding to the fasteners to engage the fluid path cover 820 with the housing cover 800 and prevent rotation.

Figure 8B:
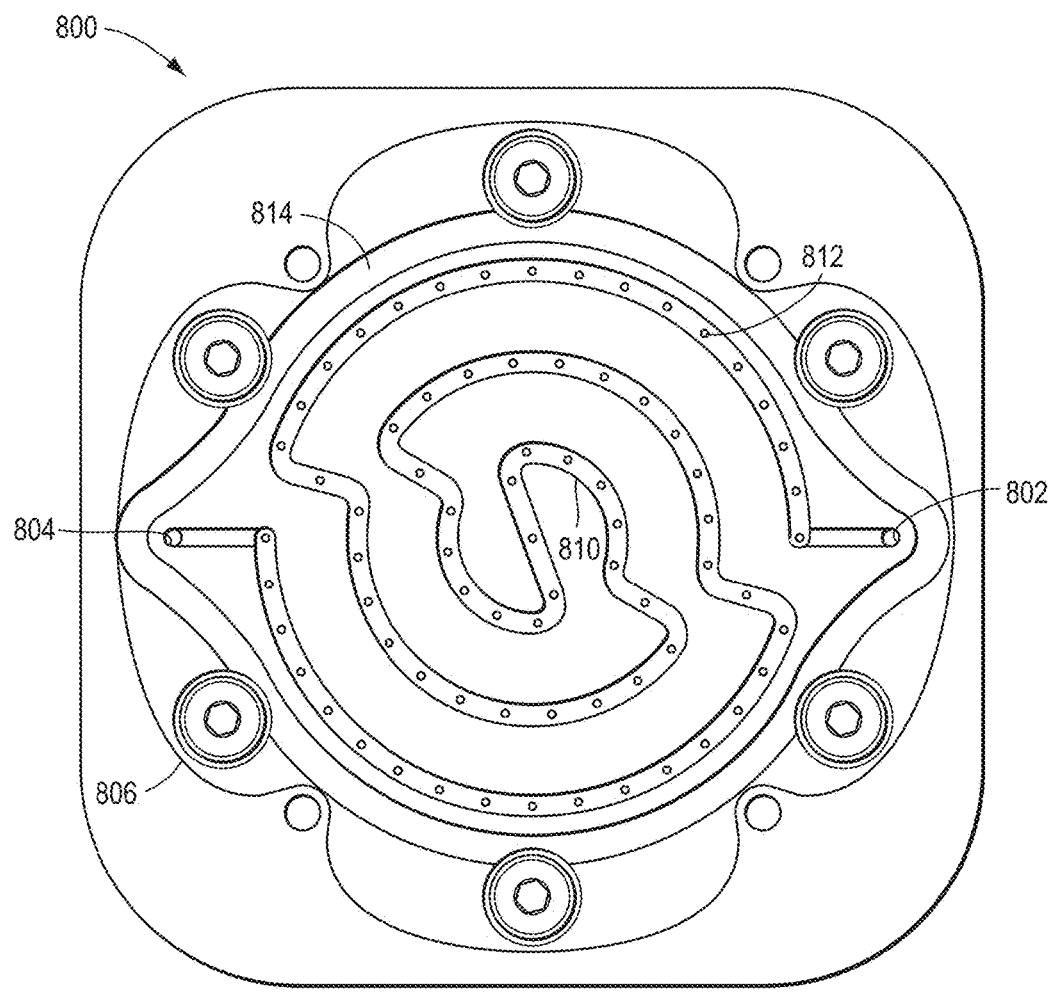
FIG. 8B is a plan view describing an example fluid path.

FIG. 8B is a top plan view describing an example housing cover 800 and fluid path 810 with the fluid path cover removed. The housing cover 800 includes a fluid path 810 that extends from a cover fluid inlet 802 to a cover fluid outlet 804 and includes a plurality of holes 812 throughout the length of the fluid path 810 that allow fluid to flow between the channel and the diaphragm below housing cover 800. A gasket 814 can be provided to enclose the fluid path 810 and prevent fluid from leaking out of the housing cover 800. A plurality of fasteners 806 can fit into corresponding fastener holes 807 (illustrated in FIG. 8C) in the housing cover 800 and can also secure the gasket 814 to the housing cover 800.

Figure 8C:
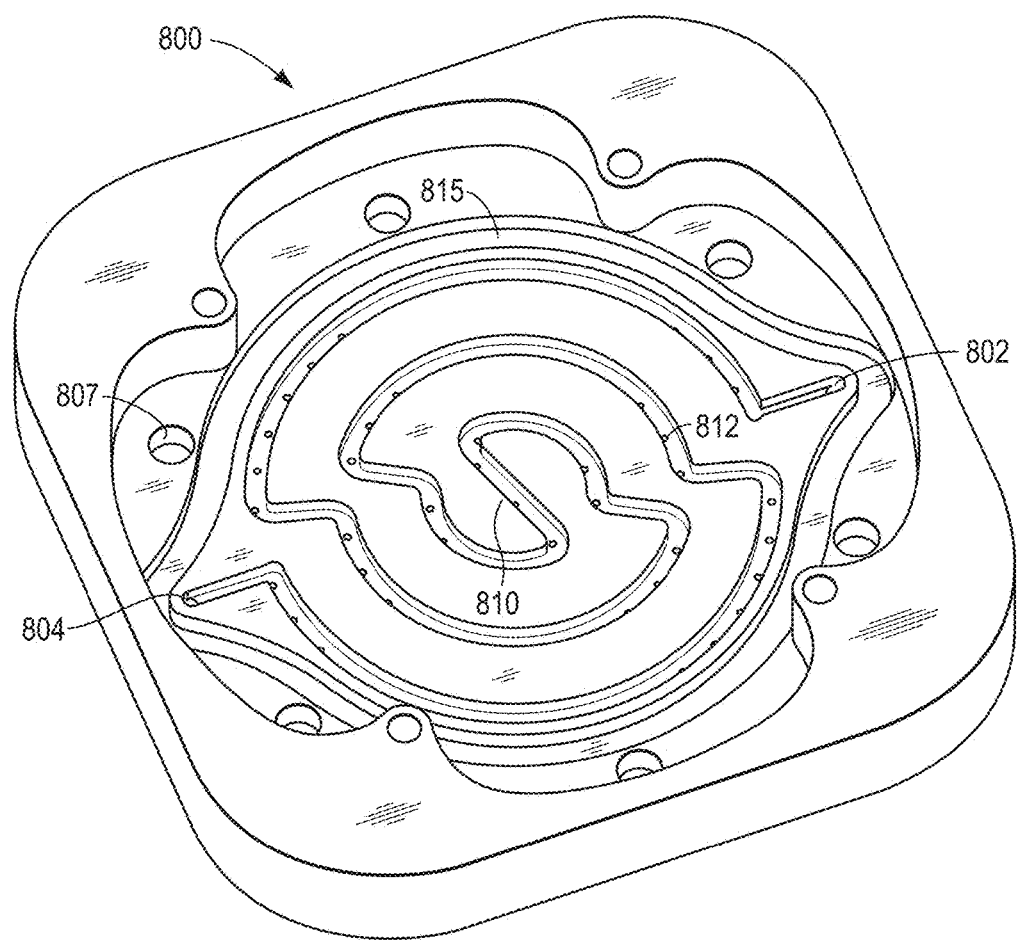
FIG. 8C is a perspective view describing an example fluid path.

FIG. 8C is a top perspective view of the housing cover 800 illustrated in FIG. 8B with the fasteners and gasket removed. A set of fastener holes 807 are provided for corresponding fasteners 806 (illustrated in FIG. 8B) to secure the housing cover 800 to a housing base. A gasket 814 can be secured in a gasket recess 815 of the housing cover 800. Cover fluid inlet 802, cover fluid outlet 804, fluid path 810 and holes 812 can be similar to those discussed above in FIGS. 8A-8B.

Figure 8D:
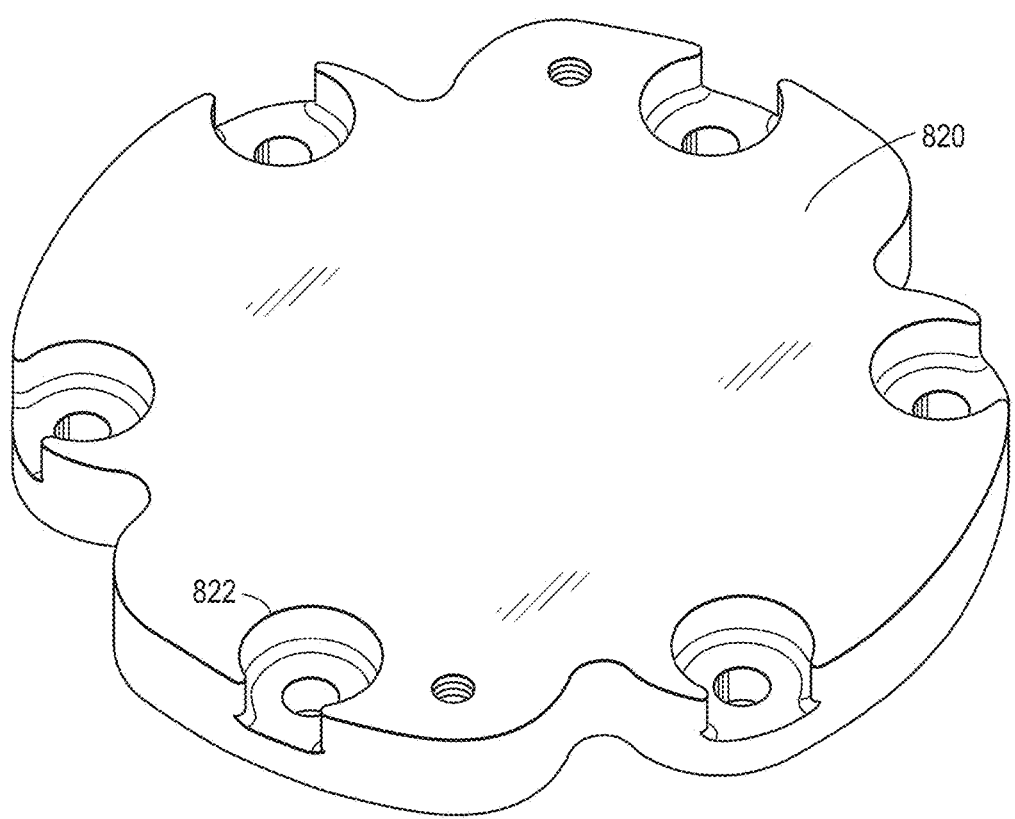
FIG. 8D is a perspective view describing an example fluid path cover.

FIG. 8D is a perspective view describing an example fluid path cover 820. The fluid path cover 820 is shaped to fit over the housing cover 800 (illustrated in FIG. 8C) and prevent fluid from leaking out of the top of the fluid path 810 (illustrated in FIG. 8C). In FIG. 8D, the fluid path cover 820 can be secured to the housing cover 800 by recesses 822 corresponding to the shape of a fastener 806 to secure the fluid path cover 820 to the housing cover 800 (illustrated in FIG. 8C).

Figure 8E:
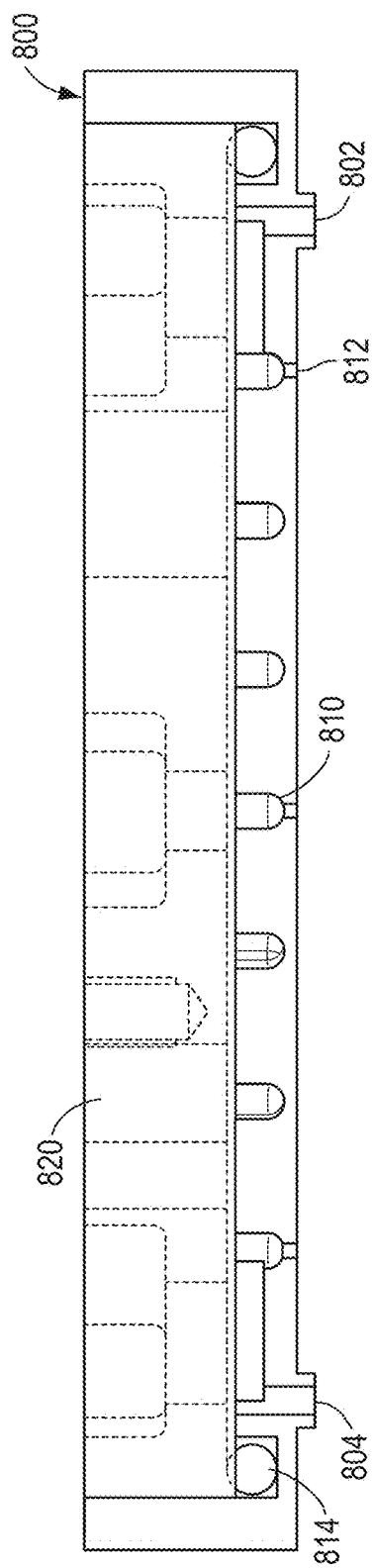
FIG. 8E is a cross-sectional view describing an example assembled housing cover.

FIG. 8E is a cross-sectional view describing an example assembled housing cover 800 and fluid path cover 820. The fluid path cover 820 is secured above the housing cover 800 such that fluid does not spill out from above the fluid path 810. Instead, fluid flows in and out of the fluid path 810 via the holes 812. The fluid that is within the fluid path 810 is further contained by the gasket 814. Cover fluid inlet 802, cover fluid outlet 804, fluid path 810 and holes 812 can be similar to those discussed above in FIGS. 8A-8B.

In an exemplary application, a fluid flow system can be calibrated using the pinch valve regulator. Calibration of the valve in a fluid flow system provides an understanding of the behavior of the valve relative to the resistance of the system coupled therewith. Fluid resistance within the system can cause pressure drop, particularly through restrictive structures, such as valves and restrictors downstream from the pinch valve regulator. In an example, the downstream fluid resistance can be determined using the pinch valve regulator. For example, with reference to FIG. 3A and FIG. 3B, a wash solution is supplied to the base fluid inlet 332 at a measured pressure (e.g., approximately 12 psi) and a reference gas pressure is supplied to the gas inlet 330, for example, at a measured gas pressure (e.g., approximately 1-2 psi). The fluid path of the diaphragm 360 fills with an equilibrium wash solution volume and a flow rate (e.g., approximately 40 µL/s) is output from the valve 300.

When an upstream fluid valve is closed and the reference gas pressure line is isolated from a gas pressure source, the gas pressure in the lower cavity 312 drives the wash solution volume in the upper cavity above the diaphragm 360 and in the fluid path 370 out of the pinch valve regulator through the cover fluid outlet 338. The volume of the reference gas increases to displace the wash volume leaving the valve.

With the upstream fluid valve closed and the reference gas pressure line isolated from the gas inlet 330, the gas pressure can be determined from a pressure sensor on the reference gas pressure line (not shown). Gas expansion in the lower cavity within the housing base leads to a small pressure decay on the gas pressure, for example, consistent with ideal gas law behavior where the product of pressure and volume is conserved. With knowledge of the absolute atmospheric pressure and total initial volume of the lower cavity and reference gas line, a pressure decay curve allows computation of resistance, and hence the flow rate of the wash volume during normal operation.

Another method of calibrating a fluid flow system using the pinch valve regulator is described below. The wash solution is supplied to the base fluid inlet 332 from a pressurized chamber (not shown) having a headspace that drives the wash solution out of the chamber and through the valve. A reference gas pressure is supplied to the gas inlet 330 and the headspace is pressurized at a set pressure. The initial volume and pressure of the headspace of the chamber is measured. The chamber is isolated from the pressure source, while maintaining the reference gas pressure in the lower cavity of the valve. Thereafter, the headspace increases in volume and reduces in pressure as the wash solution is driven from the chamber. A final pressure of the chamber is measured and the final volume can be estimated. The initial and final volumes and pressures are used to determine the resistance. During operation, the flow rate of the fluid can be determined using the resistance.

The valve thus can provide accurate and precise control of pressure that can be measured and calibrated with direct use of the valve. Diagnostics and calibration can be performed by operating the valve.

Figure 9:
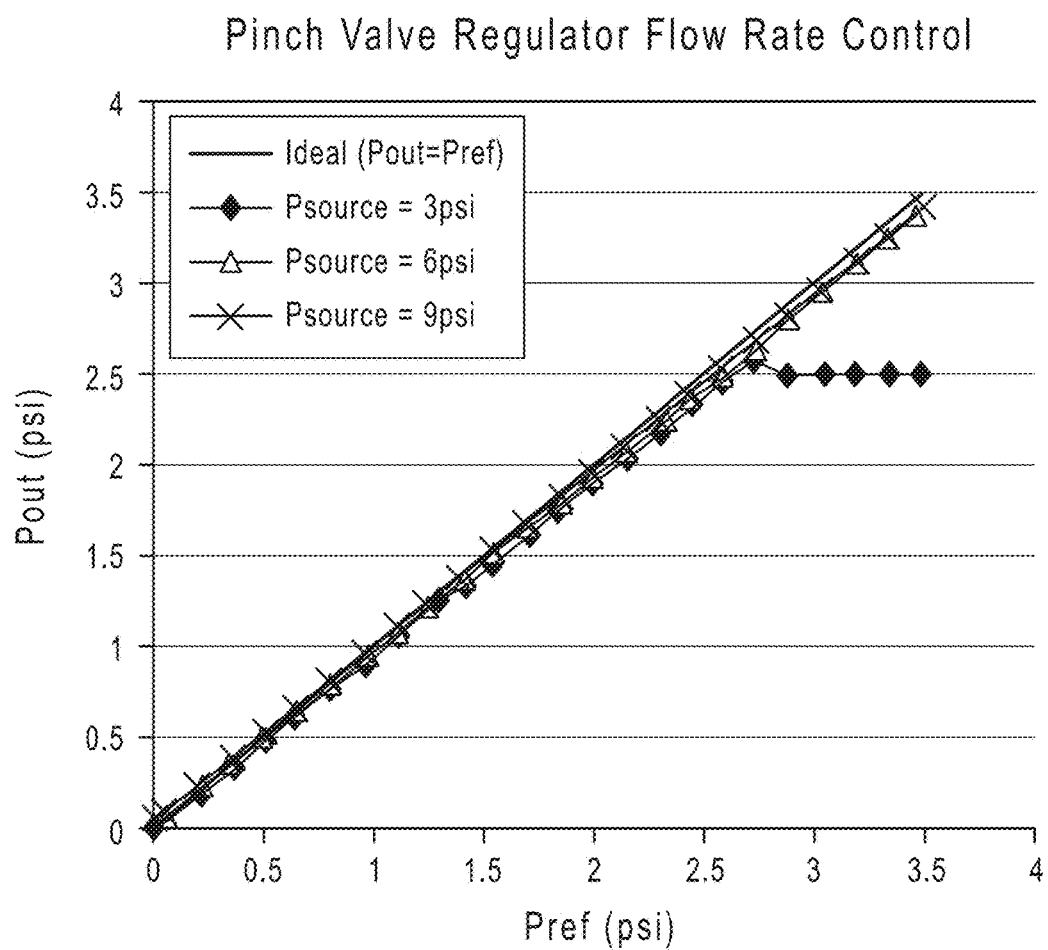
FIG. 9 is a graph describing performance of an example valve.

FIG. 9 is a graph illustrating the performance of an example valve. FIG. 9 illustrates the relationship between the reference gas pressure (Pref) against the output liquid pressure (Pout) for a set of different input liquid pressures (Psource). The linear behavior is illustrated where the output liquid pressure responds linearly to the reference gas pressure when the reference gas pressure is in a range of 0% to 90% of the input liquid pressure.

Exemplary pinch valve regulators are useful in chemical or biological processes where reagents are delivered to one or more reactors or reaction sites. The reaction sites can be monitored by chemical, electrical or optical sensors. Exemplary systems include methods and apparatuses for carrying out DNA sequencing, and in particular, pH-based DNA sequencing. For example, in pH-based DNA sequencing, base incorporations are determined by measuring hydrogen ions that are generated as natural byproducts of polymerase-catalyzed extension reactions. DNA templates each having a primer and polymerase operably bound are loaded into reaction chambers or microwells, after which repeated cycles of deoxynucleoside triphosphate (dNTP) addition and washing are carried out. Such templates are typically attached as clonal populations to a solid support, such as a microparticle, bead, or the like, and such clonal populations are loaded into reaction chambers. In each addition step of the cycle, the polymerase extends the primer by incorporating added dNTP when the next base in the template is the complement of the added dNTP. If there is one complementary base, there is one incorporation, if two, there are two incorporations, if three, there are three incorporations, and so on. With each such incorporation there is a hydrogen ion released, and collectively a population of templates releasing hydrogen ions causing very slight changes to the local pH of the reaction chamber which is detected by an electronic sensor. In addition to sequencing, the device herein can be useful for other biological instruments that require fluid storage or delivery.

Figure 10:
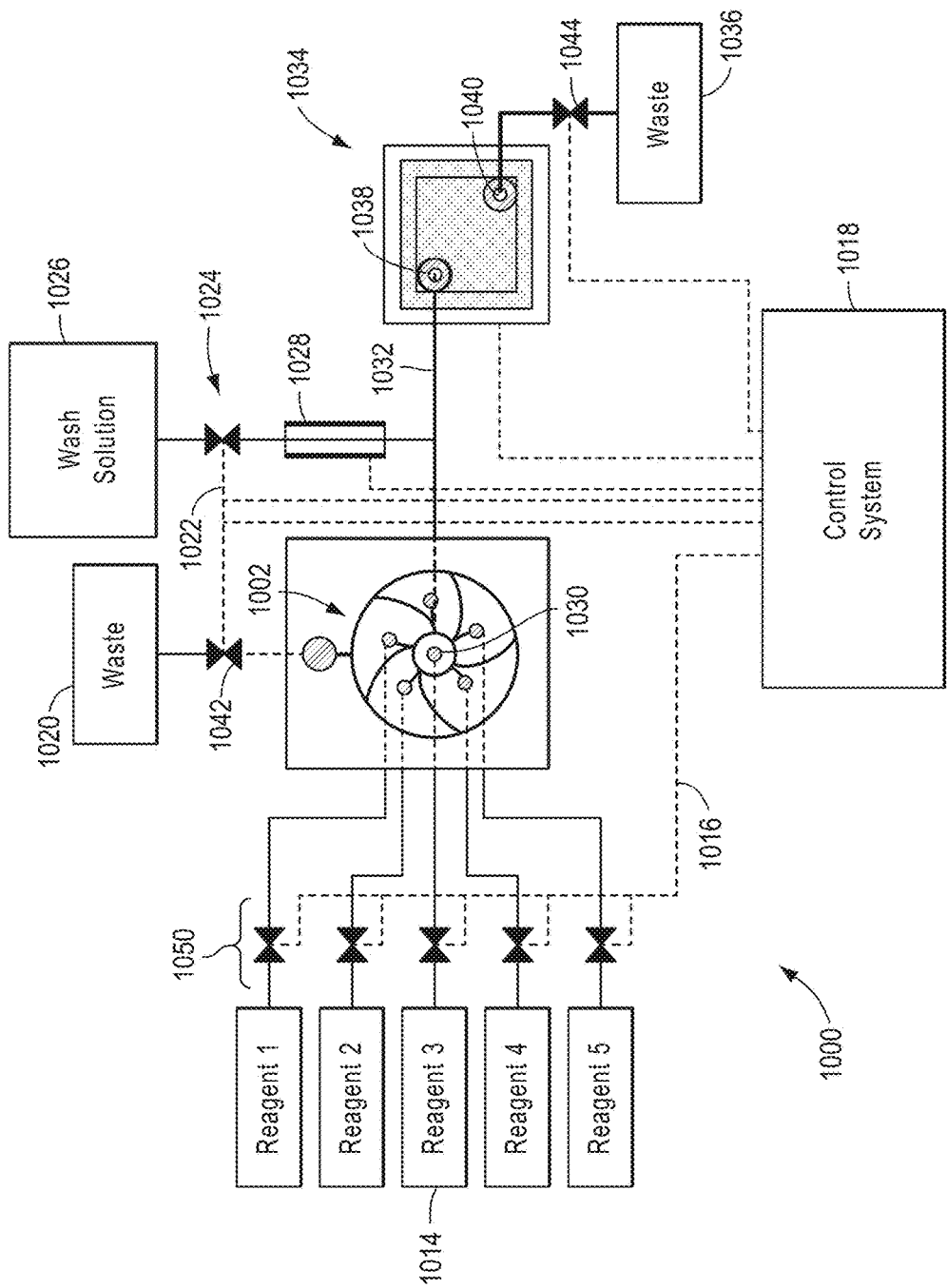
FIG. 10 is a block diagram describing an example system.

FIG. 10 diagrammatically illustrates a system employing a valve, for example, for carrying out pH-based nucleic acid sequencing. Each electronic sensor of the apparatus generates an output signal that depends on the value of a reference voltage. The fluid circuit permits multiple reagents to be delivered to the reaction chambers.

In FIG. 10, system 1000 containing fluidics circuit 1002 is connected by inlets to at least two reagent reservoirs 1014, to waste reservoir 1020, and to biosensor 1034 by fluid pathway 1032 that connects fluidics node 1030 to inlet 1038 of biosensor 1034 for fluidic communication. Reagents from reservoirs 1014 can be driven to fluidic circuit 1002 by a variety of methods including pressure, pumps, such as syringe pumps, gravity feed and the like, and are selected by control of valves 1050. Reagents from the fluidics circuit 1002 can be driven through the pinch valve 1042 receiving signals from control system 1018 to waste container 1020. Reagents from the fluidics circuit 1002 can also be driven through the pinch valve 1044 receiving signals from the control system 1018 to the waste container 1036. Control system 1018 includes controllers for valves 1050, and pinch valves 1042, 1044, that generate signals for opening and closing via electrical connection 1016.

Control system 1018 also includes controllers for other components of the system, such as wash solution valve 1024 connected thereto by electrical connection 1022, and reference electrode 1028. Control system 1018 can also include control and data acquisition functions for biosensor 1034. In one mode of operation, fluidic circuit 1002 delivers a sequence of selected reagents 1, 2, 3, 4, or 5 to biosensor 1034 under programmed control of control system 1018, such that in between selected reagent flows, fluidics circuit 1002 is primed and washed, and biosensor 1034 is washed. Fluids entering biosensor 1034 exit through outlet 1040 and are deposited in waste container 1036 via control of pinch valve regulator 1044. The valve 1044 is in fluidic communication with the sensor fluid output 1040 of the biosensor 1034.

The housing components can be constructed from a variety of materials, including metals, glass, ceramics, polymers, or the like. In an example, the material can be a transparent material, such as polycarbonate, polymethyl methacrylate, or the like.

As mentioned above, fluidic circuits can be fabrication by a variety of methods and materials. Factors to be considered in selecting materials include degree of chemical inertness required, operating conditions, e.g. temperature, and the like, volume of reagents to be delivered, whether or not a reference voltage is required, manufacturability, and the like. For meso-scale and larger scale fluid deliveries, conventional milling techniques can be used to fabricate parts that can be assembled into fluidic circuits. In one aspect, plastics such as polycarbonate, polymethyl methacrylate, and the like, can be used to fabricate fluidics circuits.

In one aspect, a valve includes a housing base defining a lower cavity, with the housing base including a pinch structure within the lower cavity, a gas inlet providing external access to the lower cavity, a base fluid inlet, and a base fluid outlet. A housing cover defines an upper cavity and includes a cover fluid inlet and a cover fluid outlet. The cover fluid inlet is in fluidic communication with the base fluid outlet between the upper cavity and the lower cavity. The cover fluid outlet provides external access from the upper cavity. A diaphragm is disposed between the housing base and the housing cover and fluidically separates the lower cavity from the upper cavity. A pinch plate is disposed in the lower cavity and includes a pinch point disposed opposite the pinch structure. A pinch tube is provided in fluidic communication between the base fluid inlet and the base fluid outlet in the louver cavity, where the pinch tube extends between the pinch structure and the pinch point.

In a related aspect, the diaphragm is to motivate the pinch point relative to the pinch structure in response to a difference between a fluid pressure in the upper cavity and a gas pressure in the lower cavity. For instance, the diaphragm is to motivate the pinch point toward the pinch structure in response to an increase in the fluid pressure within the upper cavity relative to the gas pressure in the lower cavity to restrict fluid flow in the pinch tube.

In a related aspect, a resilient structure is in contact with and provides lateral support the pinch plate. The resilient structure can include a spring. The pinch plate can include at least one pair of posts positioned on laterally opposite sides of the pinch plate, where the resilient structure engages the at least one pair of posts to provide the lateral support.

In a related aspect, the housing cover further defines a fluid path in fluidic communication with the upper cavity. The housing cover can define a fluid path having a spiral configuration extending from the cover fluid inlet and the cover fluid outlet. The housing cover can define a fluid path in fluidic communication between the cover fluid inlet and the upper cavity. The housing cover can define a fluid path in fluidic communication between the upper cavity and the cover fluid outlet. The housing cover can define a fluid path having a lower area open to the upper cavity.

In a related aspect, a pressure distributor is disposed in the upper cavity. The pressure distributor can include a filter. The filter can include a sintered metal filter. The pressure distributor can include a distributor plate. The distributor plate further defines a plurality of openings corresponding to the fluid path. A gasket can be disposed between the housing base and the housing cover. The base fluid outlet and the cover fluid inlet can be in in fluidic communication through the gasket. The base fluid outlet and the cover fluid inlet can be in fluidic communication through the diaphragm.

In another aspect, the housing cover includes a fastener fastening the housing cover to the housing base. A pressure distributor defines a projection corresponding to a shape of the fastener. The fluid path defines a lateral channel and a circular channel. The circular channel defines a plurality of grooved vertical channels. The lateral channel defines an inner island. The inner island defines a plurality of grooved vertical channels. The pressure distributor can be disposed in the upper cavity and disposed over the circular channel and the lateral channel and allow fluidic communication between the fluid path and the pressure distributor. The pressure distributor can be disposed over a portion of the circular channel and the lateral channel.

In another aspect, the fluid path can define a recess to hold a pressure distributor. A pressure distributor can prevent the diaphragm from encroaching into the fluid path. The housing cover can further define a fluid path in fluidic communication with the upper cavity and disposed opposite the upper cavity. The fluid path can further define a plurality of openings, wherein the fluid path and the diaphragm are in fluidic communication through the plurality of openings. A fluid path cover can be provided to cover the fluid path. A gasket can be disposed between the fluid path cover and the fluid path.

In another aspect, a fluid pressure at the cover fluid outlet depends linearly on a gas pressure in the lower cavity for a first range of the gas pressure to a fluid pressure at the base fluid inlet. The first range is 0% to 90% of the gas pressure to the fluid pressure at the base fluid inlet.

In another aspect, a system includes at least two reservoirs, each reservoir of the at least two reservoirs including a reagent solution. A fluid pathway is provided in fluidic communication with each of the at least two reservoirs. A biosensor is provided including a sensor fluid inlet and a sensor fluid outlet. The sensor fluid inlet of the biosensor is in fluidic communication with the fluid pathway. A valve is provided in fluidic communication with the sensor fluid outlet of the biosensor. The valve includes a housing base defining a lower cavity and the housing base including a pinch structure within the lower cavity, a gas inlet providing external access to the lower cavity, a base fluid inlet, and a base fluid outlet. A housing cover defines an upper cavity and includes a cover fluid inlet and a cover fluid outlet. The cover fluid inlet is in fluidic communication with the base fluid outlet between the upper cavity and the lower cavity. The cover fluid outlet provides external access from the upper cavity. A diaphragm is disposed between the housing base and the housing cover and fluidically separates the lower cavity from the upper cavity. A pinch plate is disposed in the lower cavity and includes a pinch point disposed opposite the pinch structure. A pinch tube is provided in fluidic communication between the base fluid inlet and the base fluid outlet in the lower cavity, where the pinch tube extends between the pinch structure and the pinch point.

In another aspect, a method of controlling fluid flow includes applying gas pressure to a gas inlet of a valve. The valve includes a housing base defining a lower cavity and comprising a pinch structure within the lower cavity, a gas inlet providing external access to the lower cavity, a base fluid inlet, and a base fluid outlet. A housing cover defines an upper cavity and includes a cover fluid inlet and a cover fluid outlet. The cover fluid inlet is in fluidic communication with the base fluid outlet between the upper cavity and the lower cavity. The cover fluid outlet provides external access from the upper cavity. A diaphragm is disposed between the housing base and the housing cover and fluidically separates the lower cavity from the upper cavity. A pinch plate is disposed in the lower cavity and includes a pinch point disposed opposite the pinch structure. A pinch tube is provided in fluidic communication between the base fluid inlet and the base fluid outlet in the lower cavity, where the pinch tube extends between the pinch structure and the pinch point. A fluid is applied to the base fluid inlet.

In a related aspect, a method of calibrating fluid flow in a valve includes measuring the pressure of the fluid applied to the base fluid inlet and the gas pressure applied to the gas inlet of the valve. A second valve provided upstream of the cover fluid outlet of the valve is closed. A gas pressure source applying the gas pressure is isolated from the gas pressure applied to the gas inlet. The isolated applied gas pressure in the lower cavity is measured. A resistance of a system coupled to the valve is determined based on the measured isolated applied gas pressure and an initial volume of the lower cavity. During operation, fluid flow rates can be determined based on the determined resistance of the valve.

In another related aspect, a method of calibrating fluid flow in a valve includes measuring a first headspace volume of a pressurized chamber coupled to the base fluid inlet, the pressure of the fluid applied to the base fluid inlet, and the gas pressure applied to the gas inlet of the valve. Pressurization to the chamber is turned off and a second pressure of the chamber and a second headspace volume is measured. A resistance of a system coupled to the valve is determined based on the measured first headspace volume, the second headspace volume, the fluid pressure and the second pressure. A fluid flow rate is determined based on the determined resistance of the system.

Features of the above aspects can be interchanged in embodiments envisaged herein.

The practice of the present invention may employ, unless otherwise indicated, conventional techniques and descriptions of mechanical engineering, electronics, fluid mechanics, and materials science, which are within the skill of the art. Such conventional techniques include, but are not limited to, design and fabrication of fluidics and microfluidics devices, and the like. Specific illustrations of suitable techniques can be had by reference to the example herein below. However, other equivalent conventional procedures may, of course, also be used.

The methods and devices are particularly well suited for meso-scale and micro-scale systems, for example, systems having passage cross-sections in the range of tens of square microns to a few square millimeters, or having flow rates in the range of from a few nL/sec to a hundreds of µL/sec. In an embodiment, a pinch valve regulator can be used to regulate flow of reagents, particularly at low flow rates, such as flow rates in the range of from 100 µL/min to 5.0 mL/min. In a particular example, such a pinch vale regulators can regulate the flow of reagents at a flow rate in a range of 0.2 mL/min to 4.0 mL/min, such as 0.4 mL/min to 3.0 mL/min. In particular, the methods and devices may be microfluidic devices including passages that have effective diameters in a range of 0.1 micrometers to 500 micrometers.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:
1. A method of controlling fluid flow comprising:
 applying a gas pressure to a gas inlet of a valve, the valve comprising:
  a housing base defining a lower cavity and comprising a pinch structure within the lower cavity, a gas inlet providing external access to the lower cavity, a base fluid inlet, and a base fluid outlet;
  a housing cover defining an upper cavity;
  a diaphragm disposed between the housing base and the housing cover and fluidically separating the lower cavity from the upper cavity;
  a pinch plate disposed in the lower cavity and comprising a pinch point disposed opposite the pinch structure; and
  a pinch tube in fluidic communication between the base fluid inlet and the base fluid outlet in the lower cavity, the pinch tube extending between the pinch structure and the pinch point, the pinch plate to adjust the relative position of the pinch point and pinch structure in response to a pressure in the upper cavity; and
 applying a fluid to the base fluid inlet.

2. The method of claim 1, further comprising:
measuring the pressure of the fluid applied to the base fluid inlet and the gas pressure applied to the gas inlet of the valve;
closing a second valve provided upstream of the cover fluid outlet of the valve;
isolating a gas pressure source applying the gas pressure from the gas pressure applied to the gas inlet;
measuring the isolated applied gas pressure in the lower cavity;
determining a resistance of a system coupled to the valve based on the measured isolated applied gas pressure and an initial volume of the lower cavity; and
determining a fluid flow rate based on the determined resistance of the system.

3. The method of claim 2, further comprising:
measuring a first headspace volume of a pressurized chamber coupled to the base fluid inlet, the pressure of the fluid applied to the base fluid inlet and the gas pressure applied to the gas inlet of the valve;
turning off a pressurization to the chamber;
measuring a second pressure of the chamber and a second headspace volume;
determining a resistance of a system coupled to the valve based on the measured first headspace volume, the second headspace volume, the fluid pressure and the second pressure; and
determining a fluid flow rate based on the determined resistance of the system.

4. The method of claim 1, wherein the diaphragm is to motivate the pinch point relative to the pinch structure in response to a difference between the pressure in the upper cavity and a gas pressure in the lower cavity.

5. The method of claim 4, wherein the diaphragm is to motivate the pinch point toward the pinch structure in response to an increase in the pressure within the upper cavity relative to the gas pressure in the lower cavity to restrict fluid flow in the pinch tube.

6. The method of claim 1, wherein the valve further comprises a resilient structure in contact with and providing lateral support to the pinch plate.

7. The method of claim 6, wherein the resilient structure includes a spring.

8. The method of claim 7, wherein the housing cover further defines a fluid path in fluidic communication with the upper cavity.

9. The method of claim 8, wherein the fluid path defines a lateral channel and a circular channel.

10. The method of claim 9, wherein the circular channel defines a plurality of grooved vertical channels.

11. The method of claim 9, wherein the lateral channel defines an inner island.

12. The method of claim 11, wherein the inner island defines a plurality of grooved vertical channels.

13. The method of claim 9, wherein the valve further comprises a pressure distributor disposed in the upper cavity and disposed over the circular channel and the lateral channel and allows fluidic communication between the fluid path and the pressure distributor.

14. The method of claim 13, wherein the pressure distributor is disposed over a portion of the circular channel and the lateral channel.

15. The method of claim 8, wherein the fluid path defines a recess to hold a pressure distributor.

16. The method of claim 6, wherein the pinch plate includes at least one pair of posts positioned on laterally opposite sides of the pinch plate, the resilient structure engaging the at least one pair of posts to provide the lateral support.

17. The method of claim 1, wherein the valve further comprises a pressure distributor disposed in the upper cavity.

18. The method of claim 17, wherein the pressure distributor includes a membrane disposed between the diaphragm and the fluid path.

19. The method of claim 1, wherein the housing cover further defines a fluid path in fluidic communication with the upper cavity, the fluid path formed on a surface of the housing cover disposed opposite as surface of the housing cover defining the upper cavity, wherein the fluid path further defines a plurality of openings, wherein the fluid path and the diaphragm are in fluidic communication through the plurality of openings, wherein the valve further comprises a fluid path cover covering the fluid path.

20. The method of claim 1, wherein a fluid pressure at the cover fluid outlet responds linearly on a gas pressure in the lower cavity for a first range of the gas pressure to a fluid pressure at the base fluid inlet, wherein the first range is 0% to 90% of the gas pressure to the fluid pressure at the base fluid inlet.

\* \* \* \* \*